United States Patent
Hopson et al.

(10) Patent No.: US 11,944,553 B2
(45) Date of Patent: Apr. 2, 2024

(54) EXPANDING SPINAL FUSION CAGE

(71) Applicants: DePuy Synthes Products, Inc., Raynham, MA (US); Stratasys, Inc., Eden Prairie, MN (US)

(72) Inventors: Peyton Hopson, Jacksonville, FL (US); Hassan Serhan, South Easton, MA (US); Eric Buehlmann, Duxbury, MA (US); Robert Sommerich, Norton, MA (US); Thomas Gamache, Westport, MA (US); Cynthia Star, Dresher, PA (US); Philip Reeves, Wirksworth (GB); Oliver Smith, Derby (GB); David Hayden, Derby (GB); Loic Le Merlus, Nottingham (GB)

(73) Assignees: DePuy Synthes Products, Inc., Raynham, MA (US); Stratasys, Inc., Eden Prairie, MN (US)

( * ) Notice: Subject to any disclaimer, the term of this patent is extended or adjusted under 35 U.S.C. 154(b) by 49 days.

(21) Appl. No.: 17/144,782

(22) Filed: Jan. 8, 2021

(65) Prior Publication Data
US 2022/0218496 A1 Jul. 14, 2022

(51) Int. Cl.
*A61F 2/44* (2006.01)
*A61F 2/30* (2006.01)

(52) U.S. Cl.
CPC ........ *A61F 2/4455* (2013.01); *A61F 2/30767* (2013.01); *A61F 2/3094* (2013.01);
(Continued)

(58) Field of Classification Search
CPC ............................. A61F 2/4455; A61F 2/441
See application file for complete search history.

(56) References Cited

U.S. PATENT DOCUMENTS

| 5,549,679 A | 8/1996 | Kuslich | |
|---|---|---|---|
| 6,582,467 B1 * | 6/2003 | Teitelbaum | A61B 17/1615 623/17.11 |

(Continued)

FOREIGN PATENT DOCUMENTS

| GB | 2524454 B | 2/2016 |
|---|---|---|
| WO | 2004047691 A1 | 6/2004 |

(Continued)

OTHER PUBLICATIONS

3D Systems (2015). 3D Systems Introduces Fabricate 3D Printing Directly onto Textiles for Cube 3D Printer. [online] Available at: https://www.3dsystems.com/press-releases/3d-systems-introduces-fabricate-3d-printing-directly-textiles-cube-3d-printer.

(Continued)

*Primary Examiner* — Brian A Dukert
(74) *Attorney, Agent, or Firm* — Barnes & Thornburg LLP

(57) ABSTRACT

Disclosed herein are expanding spinal fusion cage embodiments including an expandable cage assembly configured to expand from a collapsed state to an expanded state in an intervertebral space when inflated with a material. The assembly can include an inflatable section defining an interior volume configured to receive the material and expand the interior volume in response to a pressure from the received material to cause the expandable cage assembly to transition from the collapsed state to the expanded state, and a stabilization section configured to restrain the inflatable section during inflation.

15 Claims, 19 Drawing Sheets

(52) U.S. Cl.
CPC ...... *A61F 2/441* (2013.01); *A61F 2002/3093* (2013.01); *A61F 2002/30985* (2013.01)

(56) References Cited

U.S. PATENT DOCUMENTS

| | | | | |
|---|---|---|---|---|
| 6,733,533 | B1* | 5/2004 | Lozier | A61F 2/441 |
| | | | | 606/279 |
| 8,632,593 | B2* | 1/2014 | Suh | A61F 2/30721 |
| | | | | 623/17.15 |
| 9,457,589 | B2 | 10/2016 | Miller et al. | |
| 9,987,055 | B2* | 6/2018 | Teisen | A61B 17/1671 |
| 2004/0220672 | A1 | 11/2004 | Shadduck | |
| 2006/0100706 | A1* | 5/2006 | Shadduck | A61B 17/7098 |
| | | | | 623/17.11 |
| 2006/0106459 | A1 | 5/2006 | Truckai et al. | |
| 2007/0093899 | A1* | 4/2007 | Dutoit | A61B 17/7097 |
| | | | | 623/17.11 |
| 2007/0276491 | A1 | 11/2007 | Ahrens et al. | |
| 2009/0177206 | A1* | 7/2009 | Lozier | A61B 17/1671 |
| | | | | 606/92 |
| 2014/0020192 | A1 | 1/2014 | Jones et al. | |
| 2014/0067066 | A1 | 3/2014 | Kuslich | |
| 2016/0185041 | A1 | 6/2016 | Lisagor et al. | |
| 2016/0340826 | A1 | 11/2016 | Tibbits et al. | |
| 2017/0056179 | A1 | 3/2017 | Lorio | |
| 2017/0120535 | A1 | 5/2017 | MacCurdy et al. | |
| 2017/0333199 | A1* | 11/2017 | Sharifi-Mehr | A61F 2/4611 |
| 2020/0306052 | A1 | 10/2020 | Richter et al. | |
| 2022/0218496 | A1 | 7/2022 | Hopson et al. | |

FOREIGN PATENT DOCUMENTS

| | | |
|---|---|---|
| WO | 2015107333 A1 | 7/2015 |
| WO | 2016085863 A1 | 6/2016 |
| WO | 2016134972 A1 | 9/2016 |

OTHER PUBLICATIONS

Aceo. 2017. Aceo Design Guidelines. [Online] Available at: https://17909-presscdn-0-38-pagely.netdna-ssl.com/wp-ontent/uploads/2017/07/ACEO_Design_Guidelines_0617.pdf.
Aceo. 2017. Aceo Drop-on-demand Technology. [Online] Available at: https://www.aceo3d.com/technology/.
Ansys. 2017. Ansys Composite Materials. [Online] Available at: http://www.ansys.com/products/structures/composite-materials.
Bhardwaj, N. and Kundu, S. (2010). Electrospinning: A fascinating fiber fabrication technique. Biotechnology Advances, [online] 28(3), pp. 325-347. Available at: http://www.sciencedirect.com/science/article/pii/S0734975010000066.
Dassault Systemes. 2017. Dassault Systemes. [Online] Available at: https://www.3ds.com/.
DePuy Synthes (2017). SMARTSET™ Bone Cements Product Information. [online] Available at: http://synthes.vo.Ilnwd.net/o16/LLNWMB8/INT%20Mobile/Synthes%20International/Product%20Support%20Material/ legacy_Synthes_PDF/DSEM-BIO-0516-0056_LR.pdf.
Hinton, T., Jallerat, Q., Palchesko, R., Park, J., Grodzicki, M., Shue, H., Ramadan, M., Hudson, A. and Feinberg, A. (2015). Three-dimensional printing of complex biological structures by freeform reversible embedding of suspended hydrogels. Science Advances, [online] 1(9), pp.e1500758-e1500758. Available at: http://advances.sciencemag.org/content/advances/1/9/e1500758.full.pdf.
Kraton. 2017. Cariflex™ polyisoprene. [Online] Available at: http://www.kraton.com/products/cariflex/cariflex.php.
Lohia Corp. 2017. Circular Looms. [Online] Available at: http://www.lohiagroup.com/circular-loom.
Long, A., Clifford, M., Harrison, P. and Rudd, C. (2001). Modelling of Draping and Deformation for Textile Composites. School of Mechanical, Materials, Manufacturing Engineering and Management University of Nottingham. [online] Available at: http://userweb.eng.gla.ac.uk/philip.harrison/publications/Conference/ICMAC2001.pdf.
MacCurdy, R .; Katzschmann, R .; Kim, Y. & Rus, D. 2016. Printable Hydraulics: A Method for Fabricating Robots by 3D Co-Printing Solids and Liquids.[online] Available at: https://groups.csail.mit.edu/drl/wiki/images/7/7c/2016_MacCurdy-Printable_Hydraulics-A_methods_for_fabricating.pdf.
Maquet.com. (2017). Maquet Getinge Group. [online] Available at: https://www.maquet.com/us/.
Materialise. 2017. Materialise Streamics. [Online] Available at: http://www.materialise.com/en/software/streamics.
MIT News. 2016. First-ever 3-D printed robots made of both solids and liquids. [Online] Available at: http://news.mit.edu/2016/first-3d-printed-robots-made-of-both-solids-and-liquids-0406.
Nervous System. 2017. Kinematics Fold Simulation. [Online] Available at: https://n-e-r-v-o-u-s.com/projects/tags/algorithm/albums/kinematics-fold/.
O'Bryan, C., Bhattacharjee, T., Hart, S., Kabb, C., Schulze, K., Chilakala, I., Sumerlin, B., Sawyer, W. and Angelini, T. (2017). Self-assembled micro-organogels for 3D printing silicone structures. Science Advances, [online] 3(5), p. e1602800. Available at: http://advances.sciencemag.org/content/advances/3/5/e1602800.full.pdf.
Pérez, J., Otaduy, M. and Thomaszewski, B. (2017). Computational design and automated fabrication of kirchhoff- plateau surfaces. ACM Transactions on Graphics, [online] 36(4), pp. 1-12. Available at: http://www.gmrv.es/Publications/2017/POT17/KirchhoffPlateau.pdf.
School of Mechanical, Materials & Manufacturing Engineering University of Nottingham. 2017. Modelling of textiles and composites. [Online] Available at: https://www.nottingham.ac.uk/research/groups/composites-research-group/documents/nottmtextcomp.pdf.
Secant Group. 2017. Textile Forming Technology. [Online] Available at: http://www.secant.com/.
University Florida News (2017). New 3D printing method promises vastly superior medical implants for millions. [online] Available at: http://news.ufl.edu/articles/2017/05/new-3d-printing-method-promises-vastly-superior-medical-implants-for-millions.php.
ViscoTec. 2017. 3D printing 3D extruders for pastes and fluids, based on endless piston principle. [Online] Available at: https://www.viscotec.de/en/industry-applications/3d-printing/.
International Search Report and Written Opinion for Application No. PCT/IB2022/050103 dated Jul. 14, 2022 (16 pages).
Khalaj, et al. "3D printing advances in the development of stents." International Journal of Pharmaceutics 609 (2021): 121153.
International Preliminary Report for Application No. PCT/IB2022/050103 dated Jul. 4, 2023 (12 pages).

\* cited by examiner

FIG. 8A
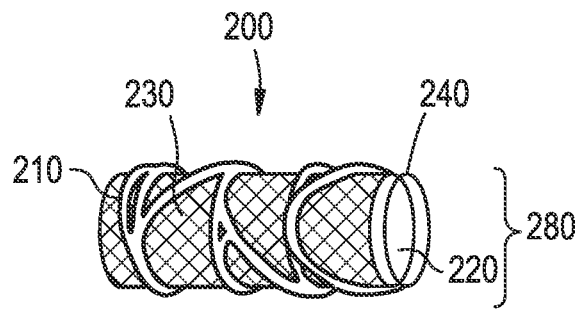
FIG. 8B
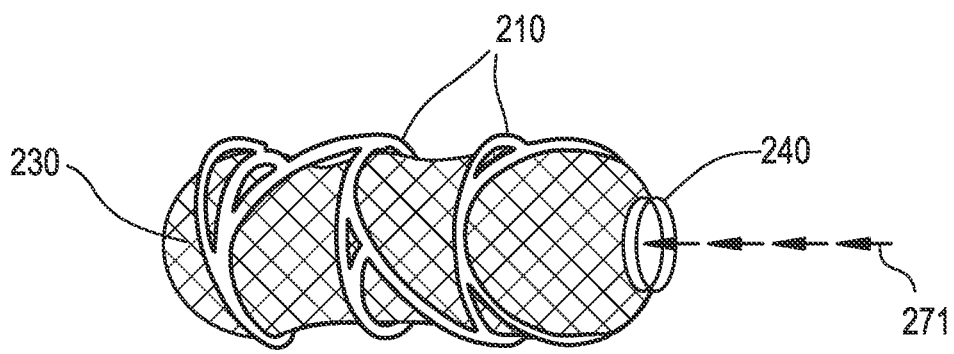
FIG. 8C
FIG. 8D
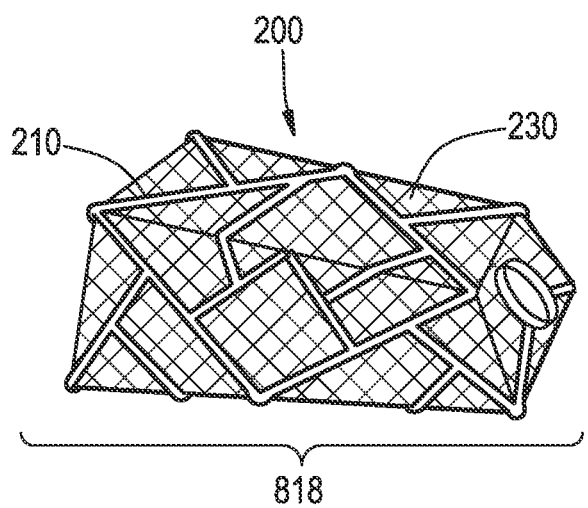
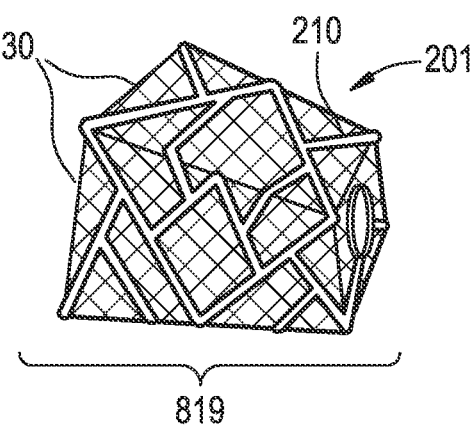

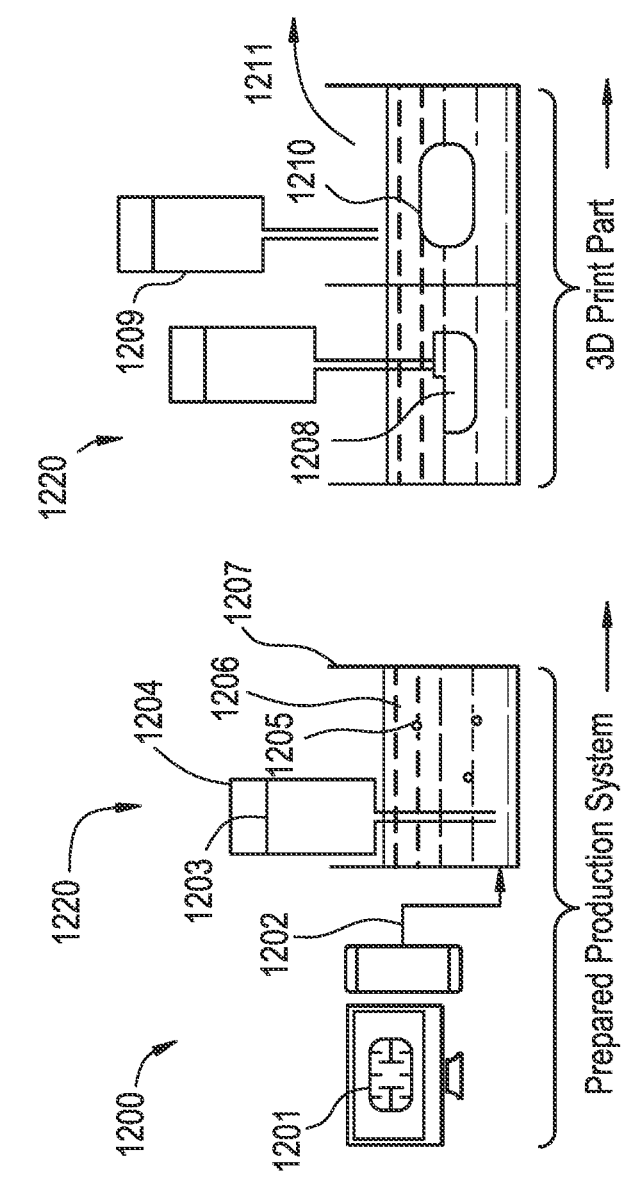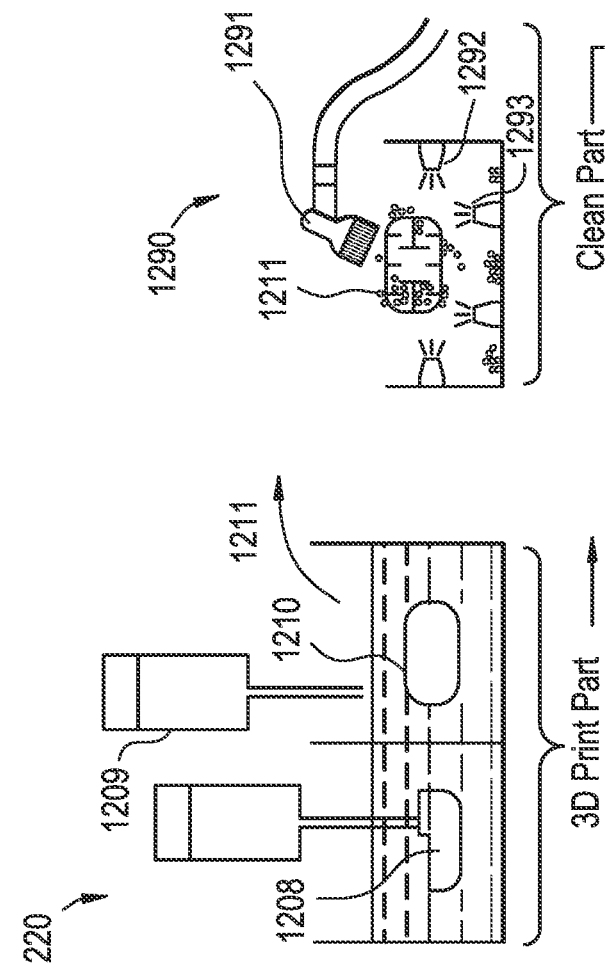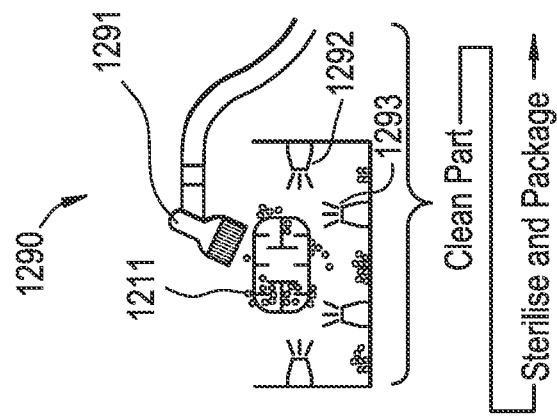

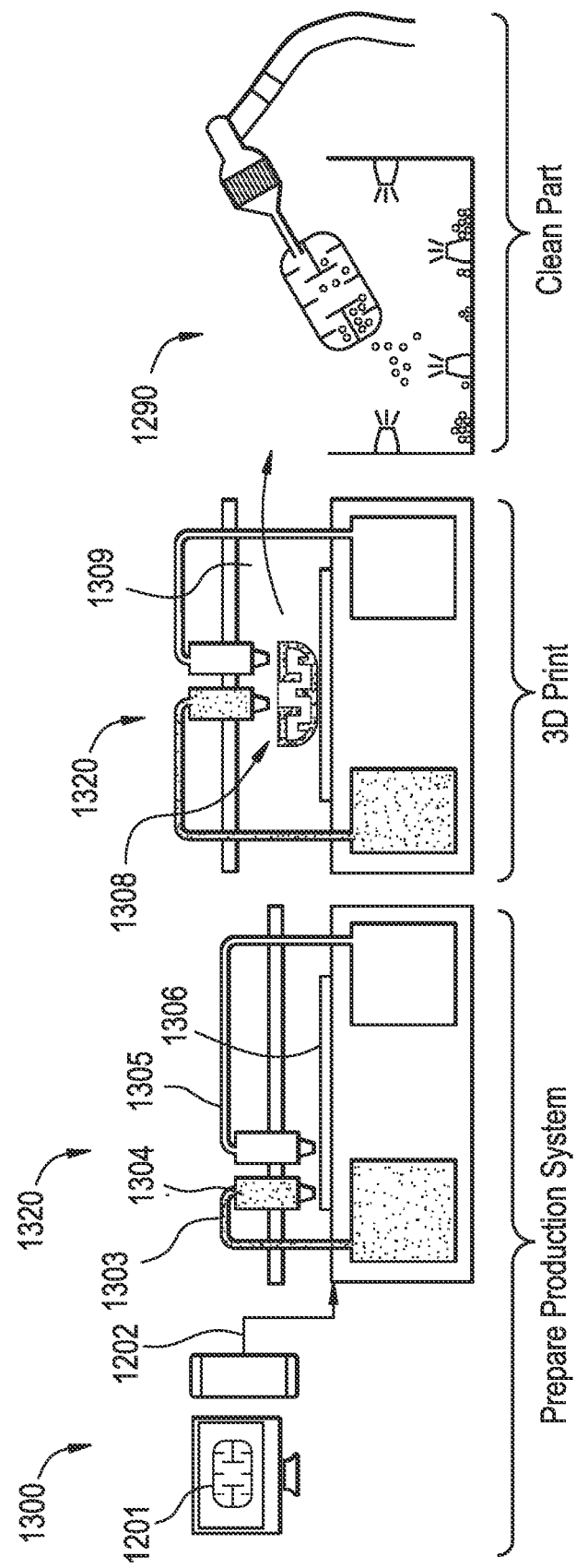

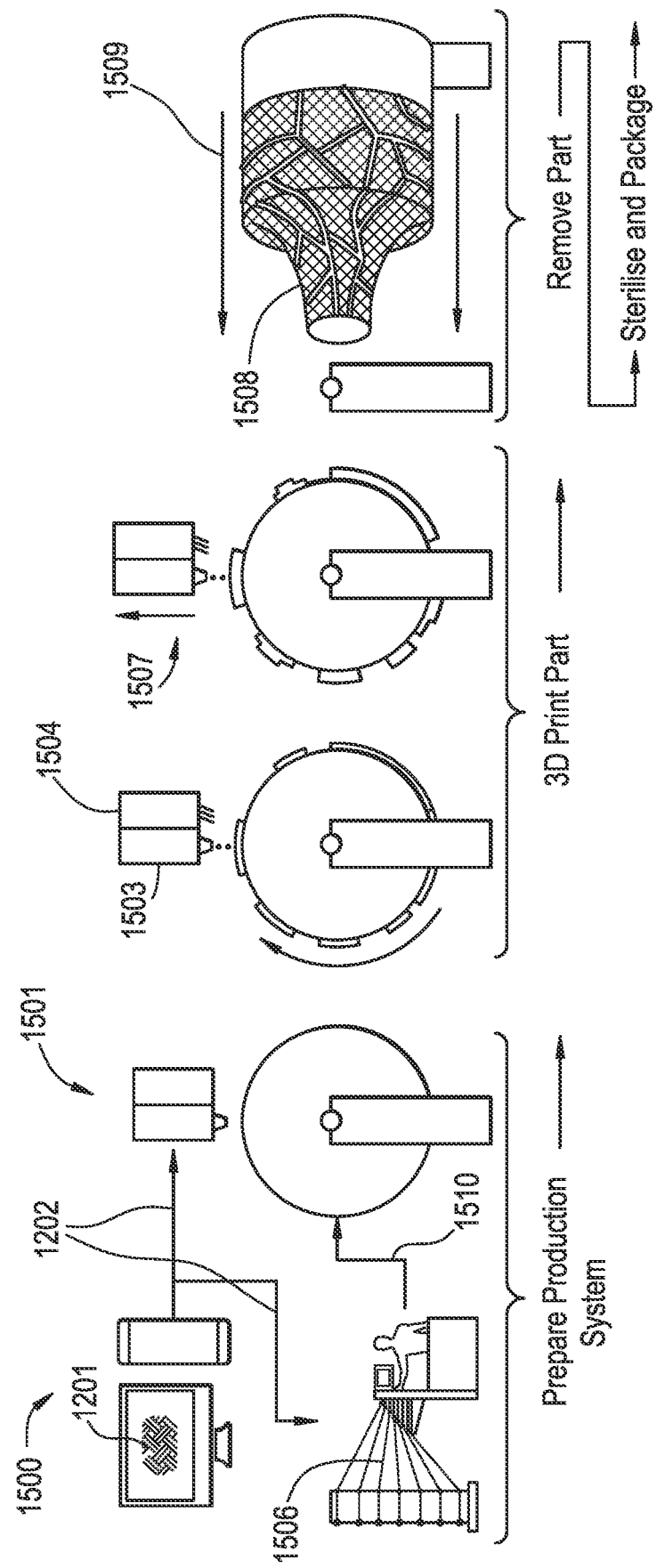

EXPANDING SPINAL FUSION CAGE

FIELD

This disclosure relates to methods and devices for stabilizing spinal motion between two adjacent vertebrae and, more particularly, to such methods and devices that utilize an expanding spinal fusion cage, which can be inserted in a collapsed state into the intervertebral space and subsequently inflated or expanded within the intervertebral space.

BACKGROUND

Minimally invasive surgical (MIS) and/or microsurgical procedures are increasingly utilized to perform spinal surgeries, such as resection, decompression, and fusion. These procedures can have a number of advantages, including reduced risk of patient injury, faster recovery time, etc. Such procedures are typically performed using various access ports or retractors that provide a passageway from the skin surface to the spine and intervertebral disc space. These ports and retractors often provide passageways of minimal size, perhaps about 30 mm in diameter or less, in order to minimize tissue trauma and successfully traverse narrow anatomical passages, such as the anatomic window of Kambin's triangle in the spine.

These minimally invasive and/or microsurgical procedures can require new instruments, devices, and methods suitable for use in the limited size passageways provided by the various ports or retractors. By way of example, certain larger devices, whether implantable devices such as fusion cages or other associated instruments, cannot be passed through a narrow opening and therefore cannot be used in minimally invasive and/or microsurgical procedures.

Accordingly, there is a need for improved surgical devices and methods, including improved spinal fusion cages, that can be utilized in minimally invasive procedures that, e.g., require passing a device through a small or restricted passageway to a surgical site.

SUMMARY

The devices and methods disclosed herein address the above-noted need by providing devices that can have a collapsed and expanded state, thereby allowing introduction through a smaller working channel while in a collapsed state and subsequent expansion at a surgical site. More particularly, the devices and methods described herein leverage advances in the ability to 3D-print or additive manufacture highly complex geometries and encapsulated structures, as well as multiple materials within a single structure, to enable the design of disc replacement devices with advanced geometries or mechanisms for expanding uniformly into a complex or asymmetrical shape through a highly controlled process.

Certain aspects of the present disclosure provide for a 3D printed spinal fusion cage that expands to a pre-defined shape and size from a compressed size in order for the spinal fusion cage to be implanted in a patient's intervertebral space through minimally invasive methods.

Two example embodiments of the present disclosure include an expanding spinal fusion cage device utilizing elastic expansion and using meta-material expansion. Other example embodiments are within the scope of the present disclosure, including, for example, implementations utilizing both elastic expansion and meta-material expansion. Additionally, other expansion configurations are described herein, and the above two example embodiments are provided only as illustrations of the present disclosure and their distinctions are presented to help explain to overall concept.

Certain aspects of the elastic expansion cage devices include, for example, a single-piece structure that contains a particular geometry to ensure controlled expansion into a defined shape and structure. For example, a soft object that can be inserted between vertebrae using current MIS methods and that can be inflated with a gas, fluid, or semi-solid material blend to expand from a simple and compressed shape into a complex, structural, and stable cage device.

Certain aspects of the meta-material expansion cage devices include, for example, a multi-material system where a bag or pouch with a surrounding 3D-printed structure that provides structural stability and control is inserted between vertebrae and inflated. For example, a mesh bag where a collapsible 3D printed structure or scaffold has been directly printed onto that mesh material acting as a physical support to the inflation of the mesh bag or pouch.

One example embodiment of the present disclosure is an expandable cage assembly configured to expand from a collapsed state to an expanded state in an intervertebral space when inflated with a material. The expandable cage assembly includes an inflatable section defining an interior volume configured to receive the material and expand the interior volume in response to a pressure from the received material to cause the expandable cage assembly to transition from the collapsed state to the expanded state, and a stabilization section configured to restrain the inflatable section during inflation.

In some instances, the stabilization section at least partially surrounds the inflatable section, the stabilization section sized and shaped to define at least a portion of a periphery of the expandable cage assembly.

In some instances, the inflatable section surrounds the stabilization section and the stabilization section is coupled with the stabilization section for retaining inflatable section.

In some instances, at least one of the inflatable section and the stabilization section includes a 3D printed material. In some instances, wherein at least one of the inflatable section and the stabilization section includes a single-piece structure. In some instances, the single-piece structure includes a 3D printed material. In some instances, the inflatable section includes a woven substrate. In some instances, the stabilization section includes a 3D printed scaffold. In some instances, wherein the stabilization section includes tubular woven structures configured to be filled by the material.

In some instances, at least one of the inflatable section and the stabilization section includes a porous structure configured to allow interaction between the material and the intervertebral space.

In some instances, the expandable cage assembly defines one or more void channels, where each void channel is formed continuously though the stabilization section and the inflatable section. In some instances, the void channels are configured to receive bone graft material.

In some instances, the stabilization section includes a rigid structure. In some instances, the rigid structure defines one or more splits arranged to facilitate deflection or deformation of the stabilization section around the inflatable section when the inflatable section moves the expandable cage assembly from the collapsed state to the expanded state. In some instances, the rigid structure defines one or more sections arranged to telescopically expand when the inflatable section moves the expandable cage assembly from the collapsed state to the expanded state.

In some instances, at least one of the inflatable section and the stabilization section includes a bio re-absorbable material configured to be reabsorbed into the body after a time when fusion has taken place.

In some instances, at least one of the inflatable section and the stabilization section includes embedded organic materials configured to expedite osteointegration. In some instances, the embedded organic materials include at least one of: hyaluronic acids, collagens, proteins, patient cells from bone grafts. In some instances, at least one of the inflatable section and the stabilization section includes embedded materials configured to expedite osteointegration, for example, phosphate.

In some instances, at least one of the inflatable section and the stabilization section includes an embedded active pharmaceutical compound.

In some instances, the expandable cage assembly has an asymmetric shape in the expanded state.

In some instances, in the expanded state, a superior surface of the expandable cage assembly is oblique to an inferior surface of the expandable cage assembly.

In some instances, wherein the expandable cage assembly is formed from a plurality of materials.

In some instances, the inflatable section and the stabilization section are formed from different materials.

The intervertebral disc implant of claim 1, wherein the inflatable section includes multiple chambers, wherein each of the multiple chambers is able to be filled with the material, and wherein the expanded shape of the intervertebral disc implant is a function of which of the multiple chambers is filled with material.

The intervertebral disc implant of claim 1, including at least one additional structural component attached thereto, wherein the additional structural component is configured to improve fixation in the intervertebral space.

The intervertebral disc implant of claim 1, wherein the inflatable section includes a core inflation area configured to be filled with the material and an outer inflation area that is configured to be filled with a biologically active material.

Another example embodiment is an intervertebral disc implant, including an expandable structure configured to elastically expand from a collapsed state to an expanded state in an intervertebral space when inflated with a material, the expandable structure including a sidewall, the sidewall defining an interior chamber configured to receive the material and expand at least a portion of the sidewall elastically in response to a pressure from the received material to cause the expandable structure to transition from the collapsed state to the expanded state. The sidewall has a variable thickness over the surface of the expandable structure configured to control differential expansion rates of the structure during expansion. In some instances, the implant includes a structured lattice configured to provide a conformal shape to the sidewall at least at a given pressure. In some instances, the implant includes a damping mechanism comprising one or more independently filled lattice channels of a structured lattice.

In some instances, the expandable structure includes a porous outer layer configured to allow interaction between the material and the intervertebral space.

In some instances, the expandable structure defines, in the expanded state, one or more void channels configured to receive bone graft material.

In some instances, an outer surface of the expandable structure defines protrusions configured to increase the fixation between the outer surface and surfaces of the intervertebral space. In some instances, the expandable structure is monolithic.

In some instances, the interior chamber includes multiple chambers, wherein each of the multiple chambers is able to be filled with the material, and wherein the expanded shape of the intervertebral disc implant is a function of which of the multiple chambers is filled with material.

In some instances, the intervertebral disc implant of includes at least one additional structural component attached thereto, wherein the additional structural component is configured to improve fixation in the intervertebral space.

In some instances, the interior chamber includes a core inflation area configured to be filled with the material and an outer inflation area that is configured to be filled with a biologically active material.

Yet another example embodiment is a surgical method, including inserting a spinal fusion cage into an intervertebral space of the patient while the cage is in a collapsed state, expanding the spinal fusion cage from the collapsed state to an expanded state by injecting a volume of a flowable material into an interior chamber of an inflatable section of the spinal fusion cage, and constraining a shape of the spinal fusion cage in the expanded state using a stabilization structure coupled to the inflatable section.

Still another example embodiment, is a method for manufacturing a surgical implant, including forming an expandable substrate from a first material, and forming a stabilization structure on the substrate from a second material using an additive manufacturing process that deposits a plurality of layers of the second material on one another.

In some instances, the expandable substrate is a woven tubular structure. In some instances, the woven tubular structure is elastically expanded over a mandrel prior to forming the stabilization structure thereon. In some instances, forming the expandable substrate is performed using an additive manufacturing process. In some instances, the additive manufacturing process is any of: jetting, extruding, and fused deposition modeling, powder bed fusion, vat photopolymerization, binder jetting, material extrusion, directed energy deposition, selective laser sintering, material jetting, and sheet lamination.

In some instances, the expandable structure includes a single-piece expanding structure. In some instances, expandable state defines a first expanded shape when the expandable structure is expanded in free space and a second expanded shape when the expandable structure is expanded the intervertebral space, the first expanded shape being at least a function of the expandable structure and the pressure of the material, and the second expanded shape being at least a function of the expandable structure, the pressure of the material, and properties of the intervertebral space. In some instances, the first expanded shape is a function of a target shape of the second expanded shape in the intervertebral space. In some instances, the first expanded shape defines a first face and a second face, and wherein an orientation between the first face and the second face is a function of a target orientation of the first face and the second face in the second expanded shape.

In some instances, some or all of the components of an expanding spinal fusion cage are 3D printed using a vat extrusion process, whereby a material is extruded into a vat of suspension.

In some instances, some or all of the components of an expanding spinal fusion cage are 3D printed using a fused deposition modelling process, whereby thermoplastics are extruded onto a variety of flat or multi-planar substrates.

In some instances, some or all of the components of an expanding spinal fusion cage are 3D printed using whereby a single or combination of elastomeric and solid materials is jetted onto a variety of substrates.

In some instances, an expanding spinal fusion cage includes a 3D woven structure that is fabricated in an initial digital weaving process then integrated into a 3D printing process as the substrate for printing.

Certain aspects of the present disclosure provide advantages to surgeons and patients. For example, aspects include a cage-like device with a smaller compressed/pre-insertion volume would reduce the required incision size and thus reduce required healing time. Some aspects provide a cage-like device that expands into a final form with multiple faces at varying angles e.g. lordotic, vertical, and horizontal. Some aspects provide a new and functionally superior expanding cage device that is sufficiently divergent from prior solutions (e.g., mechanically actuated cages) and could act as platform technology for future spinal and orthopedic products.

Some aspects of the present disclosure include an expanding cage device with bio re-absorbable materials. For example, certain implementations can include a cage device with some or all of the material constructing the device being reabsorbed into the body after a time when sufficient fusion would have taken place. This a benefit over prior spinal cage products that become useless once fusion has occurred and remain as a nonfunctioning foreign object in the patient's body.

Some aspects of the present disclosure include an expanding cage device with embedded organic materials to be used in the construction of all or part of the cage device. In some examples of both the elastic and meta-material embodiments, organic materials and compounds are formulated into the printed material and/or substrate. The embedded organic materials and compounds enable opportunities for the addition of beneficial organic compounds and molecules that, in some implementations, help expedite osteointegration, such as hyaluronic acids, collagens, proteins. In some implementations, the patient's own cells (grafts) can be formulated into the printed material that comprises their personal implant. In some implementations, inorganic material, such as calcium phosphate are embedded.

Some aspects of the present disclosure include an expanding cage device with embedded medical components and active pharmaceutical ingredients. In some examples of both the elastic and meta-material embodiments, active pharmaceutical ingredients, molecules, and compounds can be formulated into the printed material and/or substrate. Implementations including embedded medical components can enable an implant to possess a secondary function as a drug delivery platform for anti-inflammatories, antibiotics, or other pharmaceuticals with the aim of reducing risks of infection and improving overall recovery time.

BRIEF DESCRIPTION OF DRAWINGS

This disclosure will be more fully understood from the following detailed description taken in conjunction with the accompanying drawings, in which:

FIGS. 8A-8D are illustrations of a metamaterial cage device embodiment showing the expansion process;

FIGS. 12A-C are illustrations of an example extrusion process for manufacturing an expanding cage device;

FIGS. 13A-C are illustrations of an example material jetting process for manufacturing an expanding cage device;

FIGS. 15A-E are illustrations of an example process for manufacturing an expanding cage device.

DETAILED DESCRIPTION

Figure 1A:
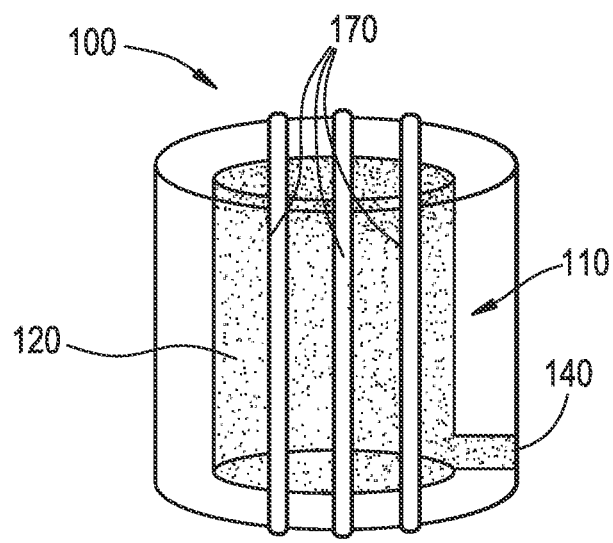
FIGS. 1A and 1B are illustrations of two different expanding spinal fusion cage embodiments according to aspects of the present disclosure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Certain aspects of the present disclosure provide for an expanding spinal fusion cage that expands to a pre-defined shape and size from a compressed size that enables the spinal fusion cage to be implanted through minimally invasive methods.

In some aspects, some or all of the components of an expanding spinal fusion cage are 3D printed. 3D printing the components, also referred to as additive manufacturing, enables the production of highly complex and/or encapsulated geometries that, in certain embodiments, provide added control to an expanding or inflating bag or balloon-like part of the expanding spinal fusion cage. Discussed in more detail below, 3D printing components of the expanding spinal cage device provides benefits, such as the production of multiple-materials at a high degree of precision within the same part and the ability to calibrate expansion behavior through variable elastic property control. Additionally, 3D printing systems can be reconfigured to print in multiple axis and on multiple substrates, which enables hybrid printing onto other functional devices, materials and substrates.

Overview

Two categories of embodiments are now described as example aspects of the present disclosure. The first category includes expanding spinal fusion cages with a structure that expands elastically. For example, a single-piece structure that contains a particular geometry to ensure the controlled expansion into a defined shape and structure. For example, a soft object that can be inserted between vertebrae using current MIS methods and that can be inflated with a gas, fluid, or semi-solid material blend to expand from a simple and compressed shape into a complex, structural, and stable cage device. The second category includes expanding spinal fusion cages that include a stabilizing structure arranged to allow the expansion of an expansion material (e.g., a woven bag or meta-material). For example, a multi-material system where a bag or pouch with a surrounding 3D-printed structure that provides structural stability and control is inserted between vertebrae and inflated. For example, a mesh bag where a collapsible 3D printed structure or scaffold has been directly printed onto that mesh material acting as a physical support to the inflation of the mesh bag or pouch. These two categories need not be distinct, and some aspects of the present disclosure include embodiments having features of both categories, for example, a stabilizing structure arranged to allow the expansion of an elastic material.

Certain aspects of the present disclosure include "two-part" systems, e.g., having an expanding spinal fusion cage/pouch element of the system, which is implanted and positioned intervertebrally, and a second major component and/or process, which is the inflation and final fixation of the device in the intervertebral space. In some instances, a secondary component can be an injectable medium used to inflate the expanding spinal fusion cage after insertion into the intervertebral space. The injectable medium can be used to provide required long-term stability and fixation of the cage (e.g., resistive force against intervertebral compression or collapse) and could be, for example, a bone cement or other suitable medium known by those skilled in the art, such as DePuy Synthes SMARTSET PMMA Bone Cement. Aspects of the present disclosure also include expanding spinal fusion cages configured to be used with the injectable mediums with added pharmaceutical compounds and/or antibiotics that increase functionality whilst potentially counter-acting any potential rejection/inflammation caused by the cage materials. Further, certain aspects include the use of 3D printed materials, in combination with elastic materials and complex geometries, to create structures that deform or expand in controlled ways.

FIGS. 1A and B are illustrations of two different expanding spinal fusion cage embodiments according to aspects of the present disclosure. FIG. 1A shows an expanding spinal fusion cage 100 that includes a body 110 defining an interior volume 120. The expanding spinal fusion cage 100 (herein also referred to as an expanding cage) is shown in an expanded state, whereby the body 110 has expanded from an initial collapsed state (not shown) as a result of an inflationary material being pumped into the interior volume 120. The body 110 also defines an access port 140 to the interior volume 120 that enables an inflationary material (e.g., a bone cement, gas, liquid, etc.) to be delivered to the interior volume 120 during an inflation operation. In some instances, the body 110 of the expanding cage 100 is configured to elastically expand from the collapsed state to the expanded state. In some instances, the body 110 of the expanding cage 100 is constructed from a single material that is configured to elastically expand the expanding cage 100 from the collapsed state to the expanded state in the intervertebral space.

Figure 1B:
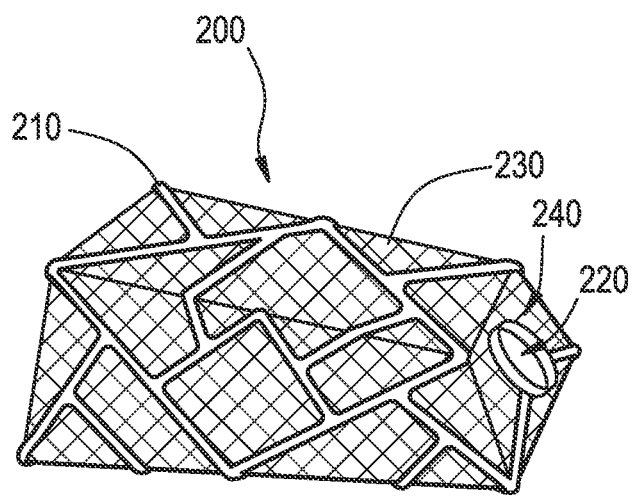

FIG. 1B shows another expanding spinal fusion cage 200 having aspects of the present disclosure. The expanding spinal fusion cage 200 includes a textile substrate 230 that defines an interior volume 220 and a stabilization structure 210 that at least partially constrains the textile substrate 230 (e.g., an expanding structure) to define an exterior size and shape of the expanding cage 200. The expanding cage 200 is shown in an expanded state, whereby the stabilization structure 210 and the textile substrate 230 has expanded from an initial collapsed state (not shown) as a result of an inflationary material being pumped into the interior volume 220. The expanding cage 200 also includes an assess port 240 to the interior volume 220 that enables an inflationary material (e.g., a bone cement, etc.) to be delivered to the interior volume 220 during an inflation operation.

In operation, after the preparation of the patient's intervertebral space to receive an implant, the expanding cage 100, 200 can be inserted into the intervertebral space in a collapsed state in order to clear the limited spatial access dimensions to the intervertebral space. After insertion, the inflationary material can be injected into the interior volume 120, 220 of the expanding cage 100 200, thereby deforming the expanding cage 100, 200 from the collapsed state to a final expanded state, where the final expanded state is not necessarily the initial expanded state of FIG. 1A because of the properties of the specific patient's intervertebral space. Instead, FIGS. 1A and 1B can illustrate one of both a "free" expansion state where the expanding cage 100, 200 is inflated outside of the intervertebral space or a "designed" expansion state, where the expanding cage 100, 200 illustrates a designed size and shape of the expanding cage 100, 200 when inflated in the intervertebral space. In some instances, the free expansion state and the designed expansion state can be different, but in other instances they can be similar. In operation, a true final shape of the expanding cage 100, 200 in the intervertebral space can be a combination of both the free and designed expansion states that depends on the geometry of the expanding cage 100, 200 and the materials the body 110 (FIG. 1A), scaffold 210, and/or textile substrate 230 (FIG. 1B) are constructed from.

Examples of Elastically Expanding Cages

Figure 2A:
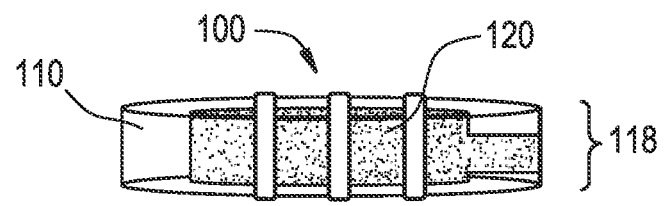
FIGS. 2A and 2B are illustrations of the collapsed and expanded states, respectively, of an elastically expanding cage device embodiment.
Figure 2B:
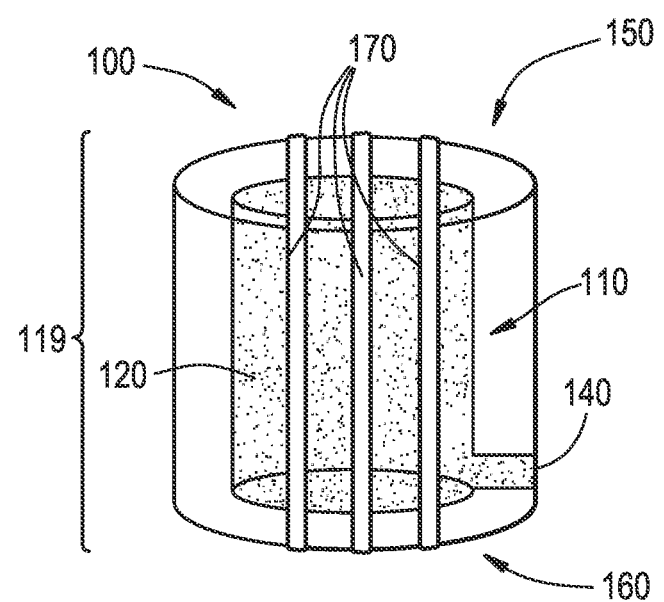

FIGS. 2A and 2B are illustrations of the collapsed and expanded states, respectively, of an elastically expanding cage device embodiment. FIG. 2A shows an expanding cage 100 in a collapsed state and FIG. 2B shows expanding cage 100 of FIG. 2A in an expanded state. In this illustration, a height 118 of the body 110 of the expanding cage 100 in the collapsed state (FIG. 2A) is reduced compared to the height 119 of the body 110 in the expanded state (FIG. 2B). In operation, an inflationary material (e.g., bone cement, etc.) can be pumped into the interior volume 120 of the body 110 in the collapsed state and the pressure of the inflationary material can deform the body 110 from the collapsed state to the expanded state, as shown in FIG. 2B.

In some instances, the body 110 can be made from a material with an elasticity sufficient to enable the expanding cage 100 to elastically expand from the collapsed state to the expanded state. In some instances, the body 110 can be constructed with a shape that allows the body 110 to be expanded and contracted with only a portion of the body being deformed. For example, the body 110 can have a bellows portion. In some instances, that body 110 can be constructed with one or more expansion joints, such that elasticity of the material of the body is not required to expand or contract the body 110. In some instances, the body can be constructed with a material having an elasticity sufficient to enable the expanding cage 100 to elastically expand from the collapsed state to the expanded state. In some instances, the elastically expanding cage 100 can also define one or more void channels 170 though the body 110 that can enable material, such as a bone graft, to be integrated with the expanding cage 100. Such channels can also permit natural growth of a patient's bone through the implant following a surgical procedure (e.g., promote the fusion process).

In some embodiments, the expanding cage 100 can be configured to be at an initially expanded state, deformed into a smaller collapsed state for insertion into an intervertebral space, and subsequently inflated into a new expanded state by the inflationary material. In some embodiments, the body 110 can be constructed with a material that is able to be elastically deformed to enable the expanding cage 100 to deformed (e.g., folded, rolled, squished, etc.) into the collapsed state. In some instances, the expanding cage 100 can be configured to be initially deformed from an initial expanded state to a collapsed state during insertion into the intervertebral space, and subsequently elastically expanded to a final expanded state that is at least partially beyond the size of the initial expanded state (e.g., at least part of the body 110 of the expanding cage 110 can be elastically expanded during an inflation operation to the final expanded shape). In some instances, the actual shape of the expanded cage 100 in the intervertebral space after the inflation operation is at least partially a function of the properties of the patient's spine (e.g., the body 110 will form to the volume and/or shape of the vertebrae), the final inflation pressure of the inflationary medium, and the material and geometric properties of the body 110 (e.g., thicker regions of the body 110 will expand less than relatively thinner region).

Figure 3A:
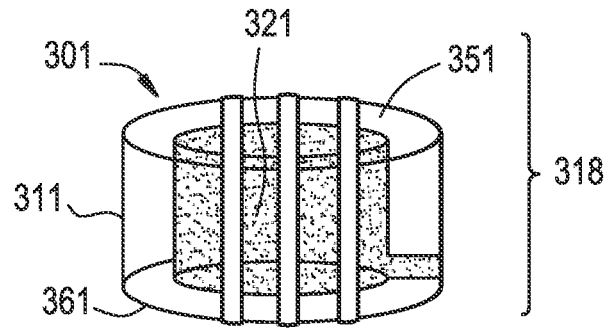
FIGS. 3A-3C are illustrations of elastically expanding cage device embodiments having different shape profiles.
Figure 3B:
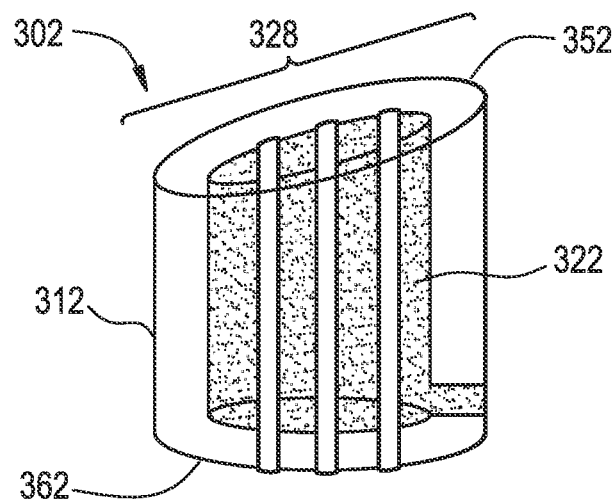
Figure 3C:
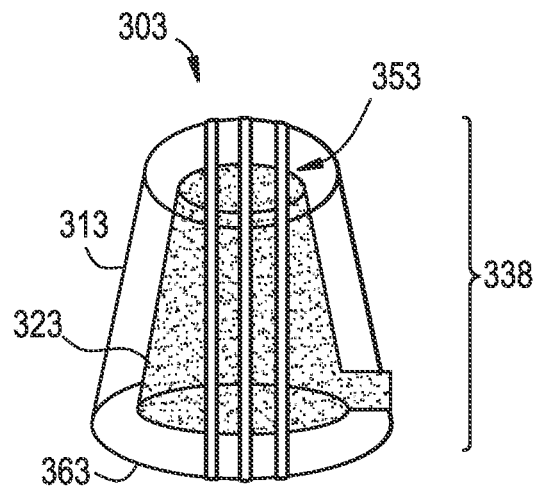

FIGS. 3A-C are illustrations of elastically expanding cage device embodiments having different shape profiles. The size and shape of the expanding cages 100, 200 are able to be configured in many different ways. For example, an expanding cage 100, 200 can have a shape that is specifically designed for a patient's bony anatomy. Also, an expanding can 100, 200 can have an expanded shape that is designed to, for example, modify the intervertebral space upon inflation or interface with an existing implant or device that is present in the intervertebral space. The following are three examples that illustrate parameters of the expanding cages 100, 200 that can be modified, but aspects of the present disclosure can be modified in many different ways and the present embodiments are only non-limiting examples of the types of parameters that can be designed or customized for a given application or patient. In some instances, the expanding cages 100, 200 can have more than one chambers for inflation, which may or may not be connected to each other. This is shown in more detail in FIGS. 10E and 10F. In some instances, multiple chambers can enable selectively filling certain of the multiple chambers to match or augment a particular shape of a patient's anatomy (e.g., their spine).

FIGS. 3A-3B illustrate different aspects of the present disclosure for providing a range of lordotic, vertical, horizontal (footprint) and face angle options depending on patient need. FIG. 3A, for example, shows an expanding cage 301 having a body 311 that is generally cylindrical in shape and defines a top face 351 and a bottom face 361 of generally the same size and orientation, with a height 318 of the body 311 spanning between the bottom face 361 and the top face 351. The expanding cage 301 is shown in the expanded state, but compared with the height 119 of expanding cage 100 of FIGS. 1A and 2B in the expanded shape, the expanding cage 301 of FIG. 3A defines a reduced height 318 that may be, for example, designed to integrate with a patient having a reduced height in their intervertebral space.

FIG. 3B shows an expanding cage 302 having a body 312 that is generally cylindrical in shape and defines a top face 352 and a bottom face 362 of generally the same size but different orientations, as compared to the arrangement in FIG. 3A. In FIG. 3B, the expanding cage 302 is shown in the expanded state and the top face 352 defines a sloped surface 382 that may be, for example, designed to integrate with adjacent vertebral surface of a patient having a similarly sloped angle with respect to the opposite vertebral surface (which would, for example, integrate with the bottom face 362 of the expanding cage 302). In other words, in some embodiments various surfaces or faces of expanding cages can be parallel with one another, while in other embodiments various surfaces or faces can be non-parallel, e.g., oblique, perpendicular, etc. to one another. In the illustrated example of FIG. 3B, by way of example, the superior or top surface 352 of the cage 302 can be oblique to the inferior or bottom surface 362 of the cage. Further, in some embodiments the cage 302 can have an asymmetric shape, or a shape that is asymmetric in at least one respect. For example, the right half of the cage 302 in FIG. 3B is not symmetrical with the left half of the cage in the view of the figure.

FIG. 3C shows an expanding cage 303 having a body 313 that is generally conical in shape and defines a top face 353 and a bottom face 363 of different sizes but similar orientations, as compared to the arrangement in FIG. 3A. In FIG. 3C, the expanding cage 303 is shown in the expanded state and defining a conical peripheral surface 338 that defines a corresponding size difference between the top face 353 and the bottom face 363.

In some instances, one or more of the height 318, slope 328, or taper 338 (or another parameter readily known to those of skill in the art) of an expanding cage can be designed as a function of a specific patient's anatomy that can be, for example, measured or determined prior to insertion of the expanding cage in order to manufacture a custom expanding spinal fusion cage for the patient.

Figure 4A:
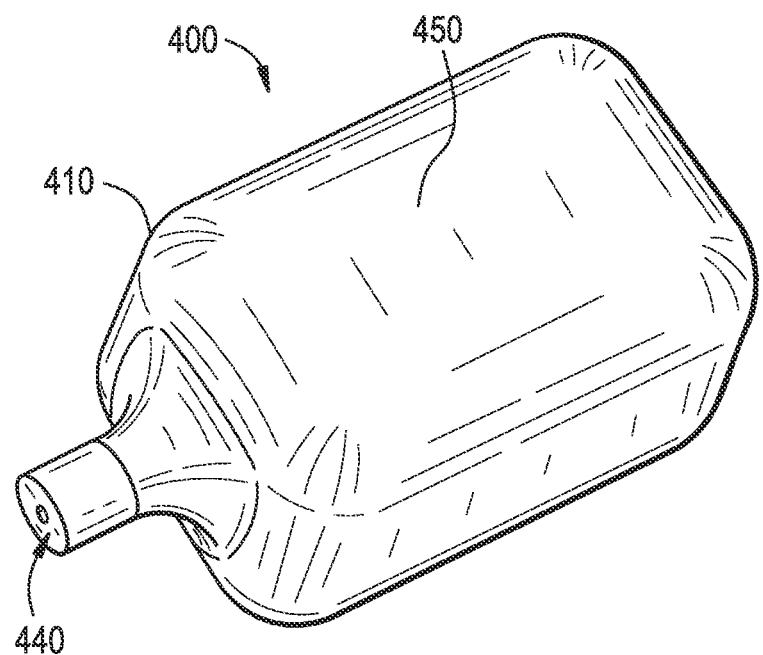
FIGS. 4A and 4B are perspective and cross-sectional views of an elastically expanding cage device embodiment.
Figure 4B:
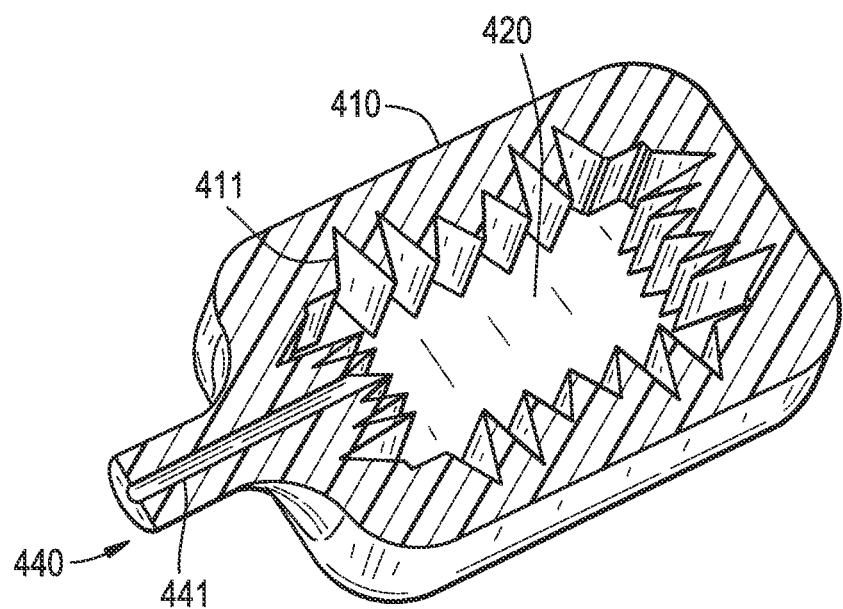

FIGS. 4A and 4B are perspective and cross-sectional views of an elastically expanding cage device embodiment in an expanded state. FIG. 4A shows an elastically expanding spinal fusion cage 400 that includes a body 410 manufactured from a material with elastic properties that enable the elastically expanding cage 400 to elastically expand from a collapsed state (not shown) to the expanded state shown in FIGS. 4A and 4B. The body 410 of the elastically expanding cage 400 defines a generally hexahedric shape with five flat faces 450 meeting at rounded corners and a sixth side defining an inflation valve 440 that is configured to permit inflationary material to be delivered to an interior volume 420 of the body 410, as shown in FIG. 4B. FIG. 4B shows the inflation valve 440 is connected to the interior volume 420 by an inflation channel the runs through the body 410. The body 410 defines a plurality of internal wall projections 411 that form the interior volume 420. The internal wall projections 411 define a variable thickness of the body 411, and the variable thickness controls differential expansion rates of the elastically expanding cage 400 during an inflation operation.

Figure 5A:
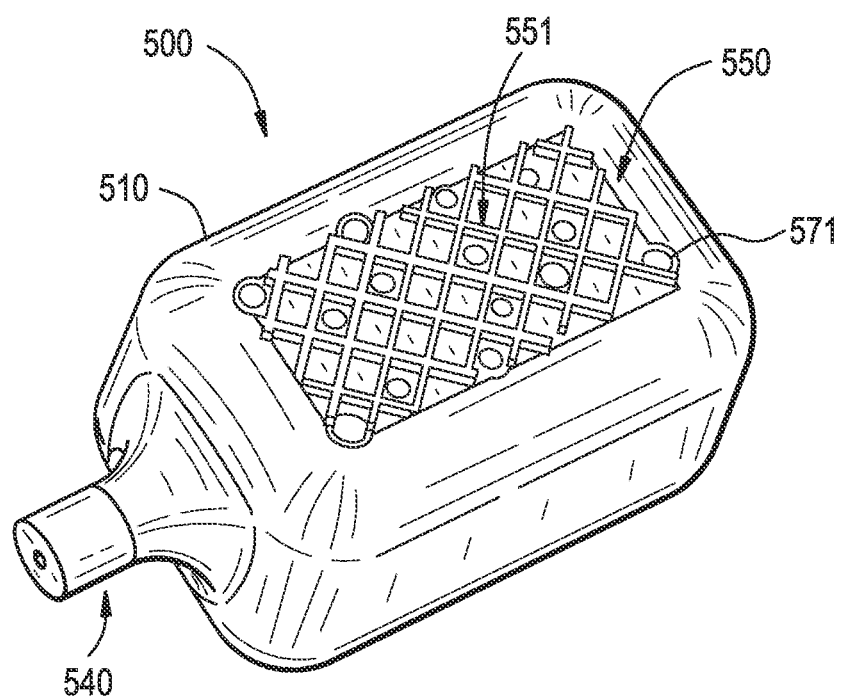
FIGS. 5A and 5B are perspective and cross-sectional views of another elastically expanding cage device embodiment.
Figure 5B:
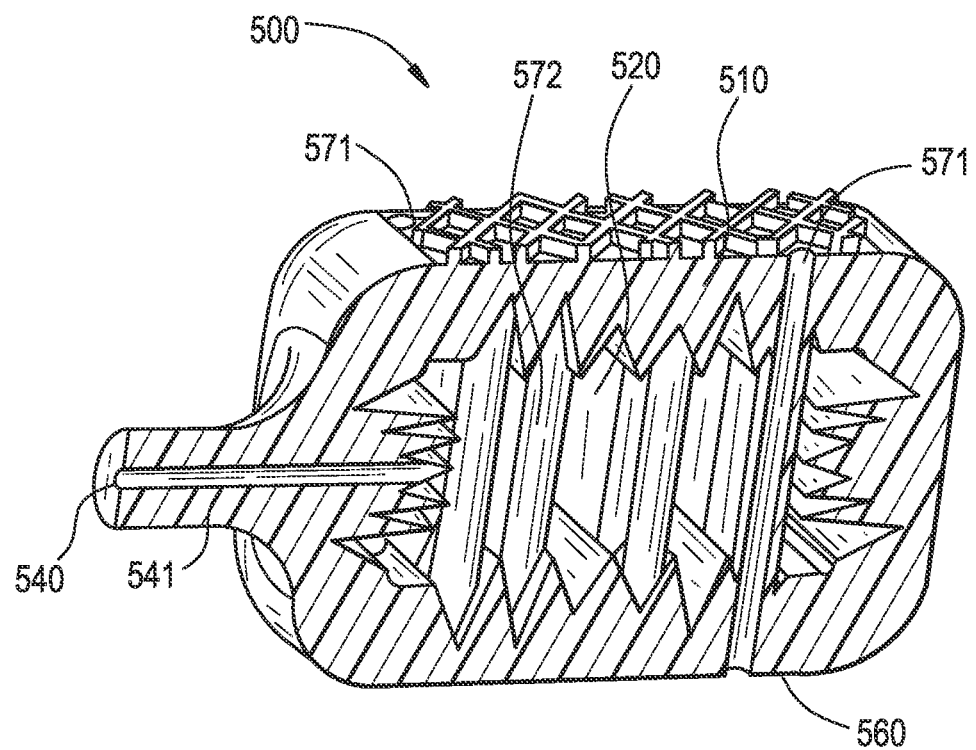

FIGS. 5A and 5B are perspective and cross-sectional views of another elastically expanding cage embodiment with additional features to enhance fixation of the expanding cage in the intervertebral space. FIG. 5A shows an elastically expanding cage 500 that includes a body 510 (e.g., a balloon) manufactured from a material with elastic properties that enable the elastically expanding cage 500 to elastically expand from a collapsed state (not shown) to the expanded state shown in FIGS. 5A and 5B. The body 510 of the elastically expanding cage 500 defines a generally hexahedric shape with five flat faces meeting at rounded corners and a sixth side defining an inflation valve 540 that is configured to permit inflationary material to be delivered to an interior volume 520 of the body 510, as shown in FIG. 5B. A top face 550 and a bottom face (560 in FIG. 5B) of the body 510 include a plurality of crisscrossed protrusions 551 that define a texture in the surface of the top face 550 that can improve fixation and prevent migration of the cage after implantation (e.g., the textured surfaces can better grip or provide more friction with vertebral endplates against which they are disposed). The cage also includes a plurality of void channels 571 that span from the top face 550 to the bottom face (560 in FIG. 5B). As noted above, these void channels can be utilized to promote bone growth through the implant, thereby speeding fusion, as well as used to pack and deliver various osteoconductive or otherwise therapeutic agents. In some instances, the body 510 is configured to have additional structural components attached thereto and configured to improve fixation in the intervertebral space. For example, top and bottom plates, such as metal and plastic components, that are affixed to the corresponding top and bottom faces of the body 510.

FIG. 5B shows the inflation valve 540 is connected to the interior volume 420 by an inflation channel 541 the runs through the body 510. The body 510 defines a plurality of internal wall projections 511 that form the interior volume 520. The internal wall projections 411 define a variable thickness of the body 511, and the variable thickness controls differential expansion rates of the elastically expanding cage 500 during an inflation operation. The body 510 also defines the plurality of void channels 571 that span between the top face 550 and the bottom face 560. As noted above, the void channels 571 can enable a direct material connection to exist across the elastically expanding cage 500 in the intervertebral space, for example, between the two opposing vertebral faces. The direct material connection can be used to, for example, allow bone graft packing and delivery of the bone graft material to the intervertebral space in order to promote ossification around the elastically expanding cage 500 after being implanted.

Figure 6A:
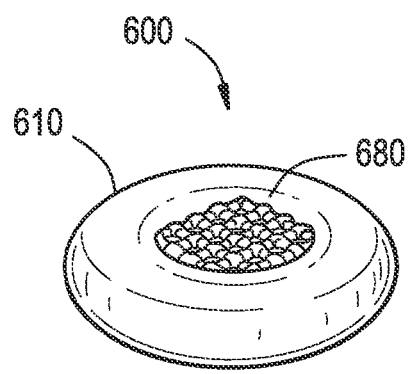
FIGS. 6A-6C are illustrations of an alternate embodiment of an elastically expanding cage device.
Figure 6B:
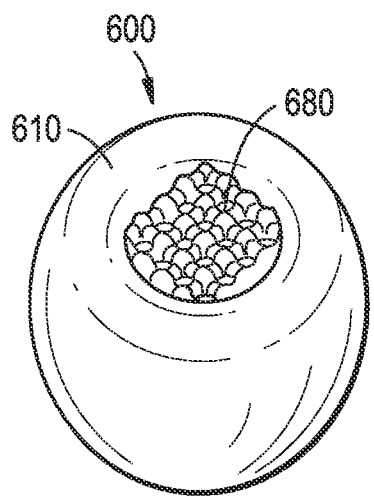
Figure 6C:
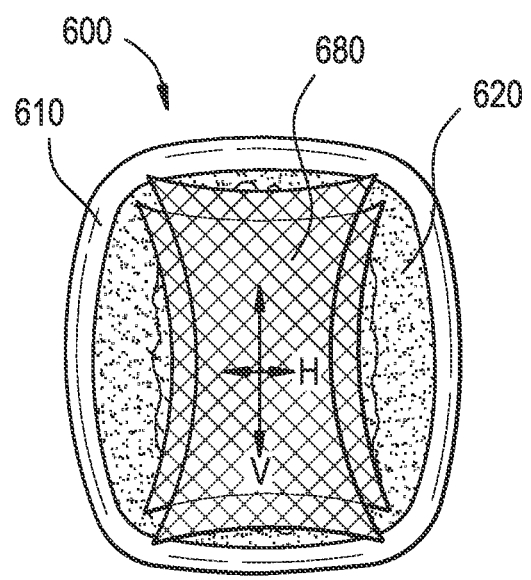

FIGS. 6A-6C are illustrations of an alternate embodiment of an elastically expanding cage device that includes a lattice structure in the center of an elastically expanding toroidal (e.g., donut shaped) body for controlling variable expansion rates and also allow eventual bone integration. FIG. 6A shows an elastically expanding spinal fusion cage 600 that includes a toroidal body 610 in a collapsed state. At the center of the body 610 is a lattice structure 680 that is coupled to the body 610. FIG. 6B shows the elastically expanding cage 600 in the expanded state, where the body 610 has expanded elastically after being filled with an inflationary medium. In some embodiments, the lattice structure 680 can be stretched or otherwise deformed during the inflation process.

In operation, the structure and material properties of the lattice structure 680 can control the expansion rate and/or final shape of body 610 by, for example, allowing more vertical expansion than horizontal expansion, or some other combination of dynamic dimensional relationships that is a function of the latticework itself and/or the connection of the body 610 to the lattice work 680. FIG. 6C shows a translucent view of the elastically expanding cage 600 with the interior volume 620 of the body being visible. FIG. 6C shows expansion of the latticework 680—and the device generally—from the initial collapsed state of FIG. 6A has occurred in the vertical direction (V) with less (or negative) corresponding expansion of the latticework 680 in the horizontal direction (H). Other constraints on the expansion of the body 610 can be achieved by varying the properties or construction of the lattice structure 680, for example, allowing horizontal expansion with limited vertical expansion.

Figure 7A:
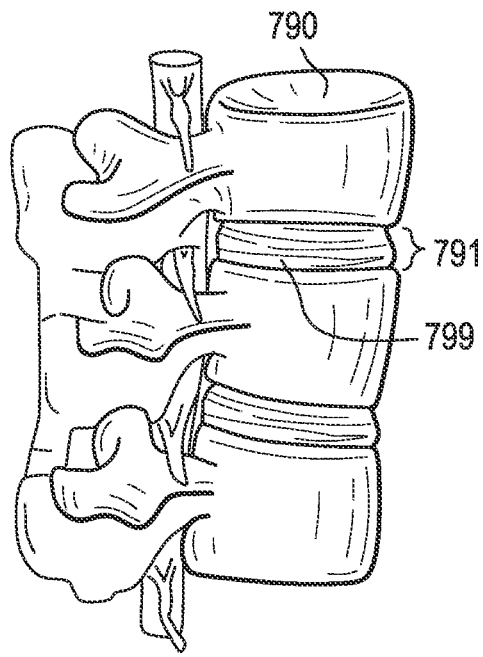
FIGS. 7A-7D are illustrations of an example procedure for replacing a spinal disc with an elastically expanding cage device.
Figure 7B:
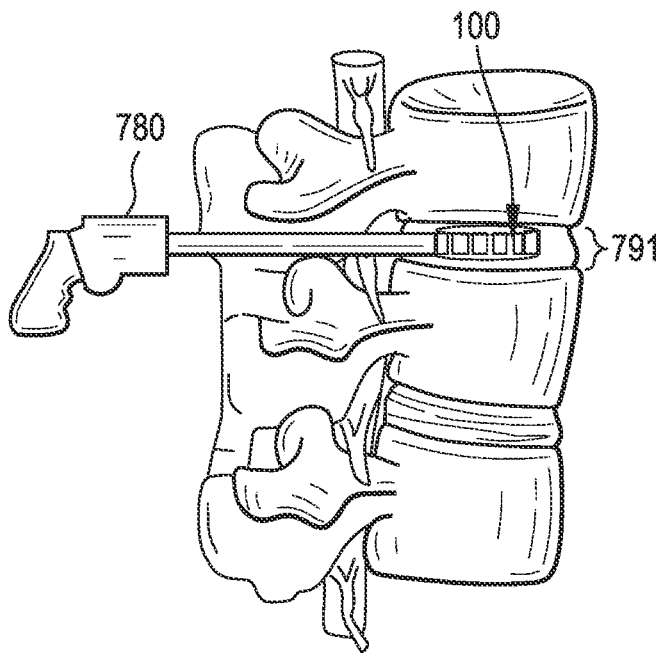
Figure 7C:
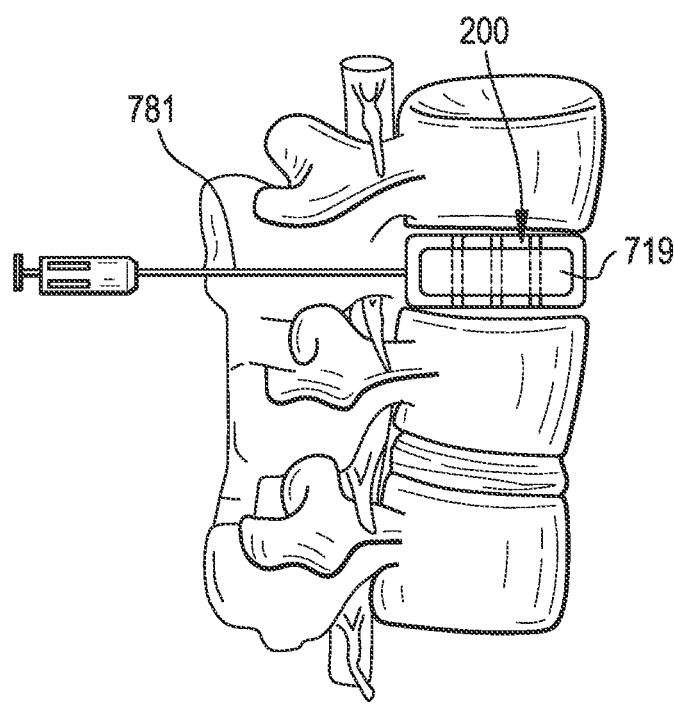
Figure 7D:
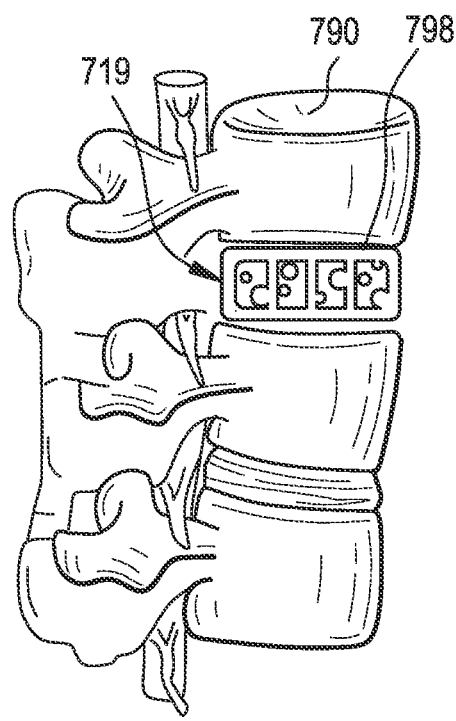

FIGS. 7A-7D are illustrations of an example procedure for replacing a spinal disc with an elastically expanding cage device. FIG. 7A shows a section of a patient's spine 790, where degenerated disc material 799 is removed from the intervertebral space 791. Next, as shown in FIG. 7B, an elastically expanding spinal fusion cage 100 is implanted while in a collapsed or constrained state and positioned in the cleared intervertebral space 791 using an implant instrument 780. Next, as shown in FIG. 7C, an inflationary medium 719 (e.g., medical cement or bone cement) is pumped into the elastically expanding spinal fusion cage 100 to cause the elastic expansion of the expanding cage 100. When the expanding cage 100 is filled with the inflationary medium 719, it can provide a solid weight-bearing structure in the intervertebral space 791. FIG. 7D shows the patient's spine 790 post-operatively, where the elastic material of the body 110 of the expanding cage 100 has bioreabsorbed over time and osteointegration has resulted in the patient's own bone matter 798 forming between the adjacent vertebrae using the cured cement 719 as a scaffold.

Example Materials

The choice of materials for the elastically expanding cage 100 embodiments is at least partially a function of the desired design requirements. For example, the material must withstand internal pressure, chemical, and heat from injected medium. In some instances, the expansion can produce up to 800N of pressure and in other instances up to 100N and others up to 1500N. In addition, the material must be elastically expandable to provide a desired expansion from the collapsed state to the expanded state. In some implementations, the body material for the elastic cage can be capable of expanding by a factor of up to about 280% without rupturing. In some instances, the elastically expanding cage 100 can be capable of withstanding up to about 25 bar of inflationary pressure. In some instances, the elastically expanding cage 100 can be capable of withstanding up to about 16,000N of pressure once in a final position and following curing of bone cement. In some instances, the materials can be less robust. For instance, the expanding cage 100 could be inflated under low pressure and then the inflation material (e.g., bone cement) is allowed to set. In this case, the expanding cage 100 would not need to withstand as high of an internal pressure as would be seen if the inflationary material were a fluid. In these cases, only the compressive stress capabilities of the material of a wall of the body would be tested as opposed to the structural integrity of the entire cage device.

In some implementations, the expanding body 110 can be configured to be manufactured in a collapsed state (e.g., a pre-expanded state) and then withstand inflation (e.g., expansion) to an expanded state without rupturing. In some implementations, the elastic body 110 can be configured to expand without rupturing when expanded in the intervertebral space. In some instances, the body 110 of the elastically expanding cage 100 can grow by more than twice the size (measured, for example, by volume or exterior linear dimensions). In some implementations, the body 110 can be configured to be manufactured in an expanded state and withstand compression into a collapsed state without splitting or otherwise failing. In some implementations, the material of the body 110 can be capable of withstanding any expected temperature or chemical factors (e.g., during sterilization) without degrading. In some implementations, the chemical factors can a function of the inflationary medium used with the body. In some implementations, the materials of the expanding cage 100 can be biocompatible, e.g., meeting the US Pharmacopeia (USP) Class VI standards for biocompatibility.

In some implementations, the material of the body 110 of the elastically expanding cage 100 can prevent the inflationary material from contaminating the implantation area or leaking uncontrollably. In some instances, the material of the body 110 can be configured to expose the inflationary medium to the body of the patient, requiring inflationary medium to be biocompatible. For example, the body 110 can include pores in the body 110 of the expanding cage 100, or the material of the body 110 itself can be a porous material.

Exemplary materials for the expanding spinal fusion cage embodiments can include polymers, which can satisfy both medical and functional requirements for the devices. For example, polyisoprene (e.g., Cariflex Polyisoprene) can meet biocompatibility requirements and exhibit high elongation properties, thereby allowing for the required factor of expansion (e.g., up to about 280%). Polyisoprene (e.g., synthetic latex) can also exhibit sufficient Young's modulus for use in the expanding cage. In some instances, a polyisoprene body 110 of an expanding cage 100 can be 3D printed using Vat polymerization and/or material jetting techniques.

Additionally, in some instances, polyisoprene can be jetted using methods that print picodot size deposits, which enable the jetted polyisoprene of the body 110 to keep its mechanical properties. In some instances, a semi-porous geometric micro-structure can be constructed within the 3D jetted polyisoprene to better engineer a rate of bioreabsorption. Polyester and PET are other biocompatible and biodegradable materials commonly used in medical applications that could be utilized in various aspects and embodiments of the present disclosure. Examples include aliphatic polyesters (e.g., PLLA, PLA, PLGA, PGA, PDS, PCL, etc.) that are known to be biocompatible and absorbable. In some instances, the added materials that are included with the printed structure are able to create a response from the surrounding tissue such that the osteointegration of the cage device is improved or made to occur faster. In some instances, the added materials can be used in small quantities through the printing process and provide a positive effect, whereas if they were used in bulk they may create other issues such as biocompatibility. In some instances, photocurable constructs (e.g., acrylate scaffolds with urethane linkages, etc.) as well as silicone materials are used in combination with or in replacement of the above materials.

3D Printing Techniques

Certain aspects of the present disclosure include methods of 3D printing some or all of the structures of an expanding spinal fusion cage according to embodiments disclosed herein. With regard to the above-identified elastically expanding cages, multiple different 3D printing techniques can be used, including, but not limited to, vat extrusion, selective laser sintering, and material jetting and stereolithography.

Examples of Expanding Cages with Meta-Materials

FIGS. 8A-8D are illustrations of one embodiment of a metamaterial cage (i.e., formed from or having hybrid characteristics of multiple materials) embodiment showing the expansion process. FIG. 8A shows an expanding cage 200 in a pre-expansion or collapsed state where the expanding cage 200 has a generally tubular shape with a minor diameter 280 that is about the same size as an inflation valve 240 disposed in the body of the expanding cage 200. In this pre-expansion state, the expanding cage 200 is sized and shaped to be able to be inserted into the intervertebral space (e.g., 791 of FIG. 7A) via existing minimally invasive surgical techniques. The expanding cage 200 can include an expanding structure that is shown as a textile substrate 230 and a stabilization structure wrapped around the textile substrate 230 that is shown as a network of 3D scaffolds 210. In some instances, the textile substrate 230 can be a woven textile substrate. The textile substrate 230 defines an interior volume 220 that can be configured to receive and inflationary medium for expanding the textile substrate 230. The textile substrate 230 can be capable of inflation to a larger size and the 3D scaffold 210 can be configured to either expand with the textile substrate 230 or otherwise allow the expansion of the textile substrate 230 until the 3D scaffold 210 constrains further expansion of the textile substrate 230.

In the collapsed state, both of the textile substrate 230 and the 3D scaffold 210 can be compressed down into a small volume to enable the expanding cage 200 to be inserted into the intervertebral space and subsequently inflated to a larger size using an inflationary medium, as shown in FIG. 8B. In some instances, the 3D scaffold can control the differential expansion rate of the textile substrate 230 during the inflation process. In some instances, the 3D scaffold can at least partially define a size and shape of the expanding cage 200 by restricting further expansion of the textile substrate 230, as shown in FIGS. 8C and 8D.

In FIG. 8B, an inflationary medium is injected (as shown by arrows 271) into the interior volume 220 of the expanding cage 200. The expanding cage 200 can be filled with the inflationary medium, and pressure from the inflationary medium can expand the textile substrate 220. As the textile substrate 230 expands within the 3D scaffold 210, the 3D scaffold also expands, grows, unfolds, or otherwise controls the expansion of the textile substrate 230. In some instances, the expanding cage 200 includes a dual inflation system, including a core inflation area that is configured to be filled with an inflationary material and an outer inflation area that is configured to be filled with an anti-inflammatory or other media for providing a biological effect.

FIG. 8C shows the expanding cage 200 in an expanded state where the pressure of the inflationary material pumped into the expanding cage 200 has reached a designed pressure and, as a result, the textile substrate 230 and 3D scaffold 210 has expanded to a designed sized and shape. FIG. 8C shows the expanding cage 200 having a given length scale 818 that is, in some instances, a function of the material properties and size and shape of the textile substrate and the 3D scaffold 210, as well as the pressure of the inflation material. For example, FIG. 8D shows another expanding cage 201 with the same textile substrate 210 as the expanding cage 200 of FIG. 8C, but with a different 3D scaffold 211 that results in a different length scale 819 of the expanding cage 201 in the expanded state. Any number of final shapes and sizes for the expanding cage 200 are possible depending on the particular construction of the textile substrate 230 and the 3D scaffold 210. In some embodiments, there are pores in an outer surface of the expanding cage 200, which, in some instances, do no open to allow material to exude into the intervertebral space until the pressure inside the expanding cage 200 reaches a threshold or final pressure.

In some instances, however, the 3D scaffold 230 can be a rigid stabilizing structure that can be configured to constrain, control, or otherwise limit the expansion and/or final shape and size of the expanding cage 200 depending on the required parameters of the expanding cage. In some instances, the textile substrate 230 can be an elastically expanding material. In some instances, the textile substrate 230 can be inelastic and can be configured to expand from a collapsed state to an expanded state by inflating from a 'crumpled' or otherwise compacted shape to a maximally volumetric shape. In some instances, the textile substrate 230 can be porous and can enable transfer of the inflationary medium across the textile substrate 230 in order to, for example, promote fusion in of the inflationary medium with the surfaces of the intervertebral space.

Figure 9A:
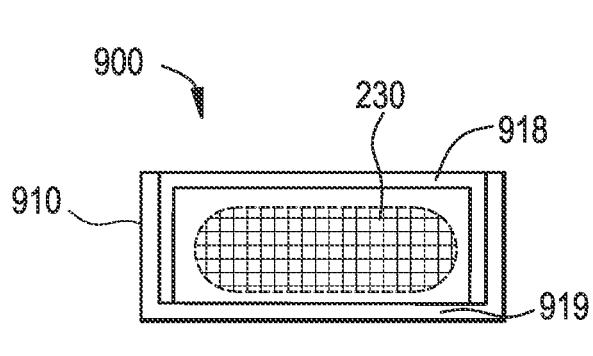
FIGS. 9A-9D are cross-sectional schematics of two alternative expanding cage device embodiments with an exterior stabilization structure.
Figure 9B:
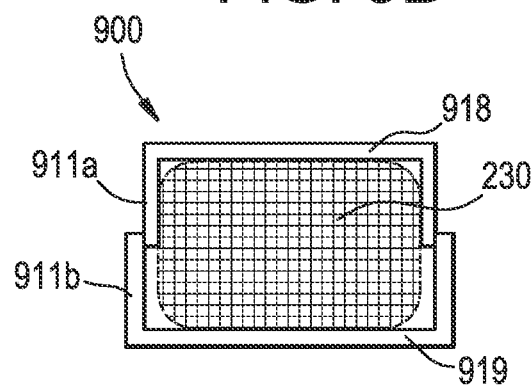

FIGS. 9A-9D are cross-sectional schematics of two alternative expanding cage device embodiments with an exterior 3D scaffold formed as a rigid exterior stabilization structure. FIG. 9A shows an expanding cage 900 with a rigid external structure 910 that at least partially surrounds a woven textile substrate 230. The rigid external structure 910 includes a rigid top container 918 and a rigid bottom container 919 that are able to expand away from each via extension coupling 910 when the woven textile substrate 230 is inflated, as shown in FIG. 9B. In some instances, the rigid top and bottom containers 918, 919 are box-like structures that slide in a single degree of freedom with respect to each other during inflation of the woven textile substrate 230, with the extension coupling 910 being the overlap between the box-like structures that is configured to prevent separation beyond, for example, the extension shown in FIG. 9B. In some instances, the rigid top and bottom containers 918, 919 are top and bottom face members that are connected by two or more individual extension couplings 910 configured to at least constrain the rigid top and bottom containers 918, 919 in the single degree of freedom of extension show in FIGS. 9A and 9B.

Figure 9C:
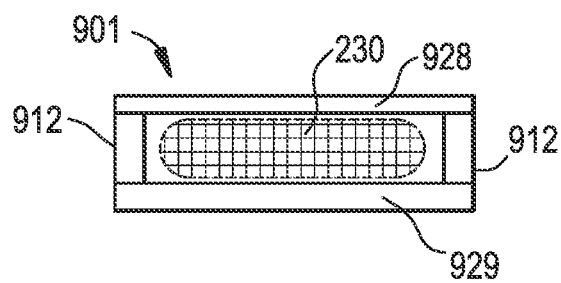
Figure 9D:
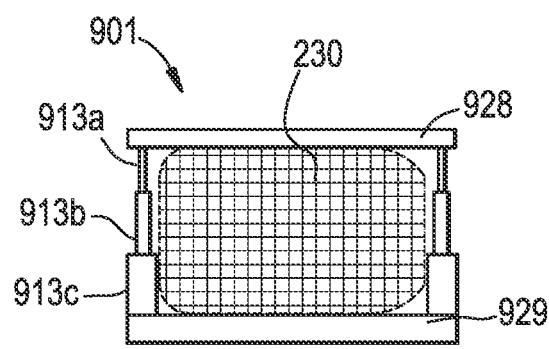

FIG. 9C shows an expanding cage 901 embodiment with ridged exterior stabilization structure that includes a rigid top element 928 connected to a rigid bottom element 929 via two or more telescopic extension mechanisms 912. The expanding cage 901 includes a woven textile substrate 230 between the rigid top and bottom elements 928, 929 that, during inflation, translates the rigid top and bottom elements 928, 929 away from each other via an extension of the telescopic extension mechanisms 912, as shown in FIG. 9D. In some instances, the telescopic extension mechanisms 912 can be made of three or more telescopic elements 913a-c to allow the rigid top and bottom elements 928, 929 to expand away from each other a distance more than twice a collapsed length of the telescopic extension mechanisms 912, as shown. The telescoping elements can either be one rectangle in rectangle telescoping element on each side or multiple cylindrical telescoping elements on each side.

Figure 10A:
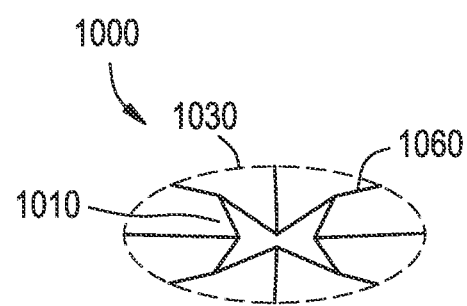
FIGS. 10A-10D are cross-sectional schematics of two alternative expanding cage device embodiments with an internal stabilization structure.
Figure 10B:
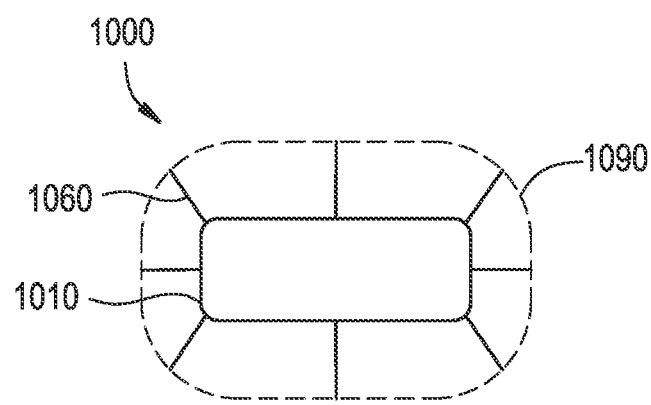

FIGS. 10A-10D are cross-sectional schematics of two alternative expanding cage device embodiments with an internal stabilization structure in the form of a scaffold to constrain the expansion and shape of an exterior woven textile substrate. FIG. 10A shows an expanding cage 1000 that includes an interior expanding scaffold 1010 surrounded an exterior woven textile substrate 1030 in a collapsed state. The exterior woven textile substrate 1030 can be connected to the interior expanding scaffold 1010 by a plurality of threads 1060. The interior expanding scaffold 1010 can be configured to expand by inflation of the exterior woven textile substrate 1030 until the interior expanding scaffold 1010 reaches a designed maximum extension size, as shown in FIG. 10B. FIG. 10B shows the expanded exterior woven textile substrate 1030 being constrained in an expanded state by the fully expanded interior expanding scaffold 1010. In operation, the shape of the fully expanded interior expanding scaffold 1010 can define the shape of the inflated exterior woven textile substrate 1030. In some instances, the expansion of the interior expanding scaffold 1010 can be configured to control the overall expansion of the expanding cage 1000.

Figure 10C:
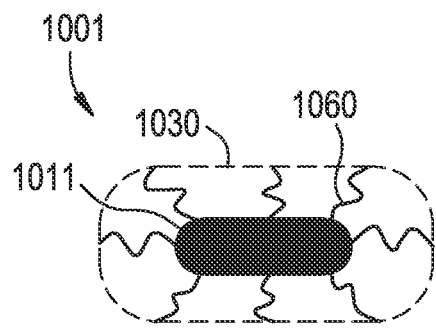
Figure 10D:
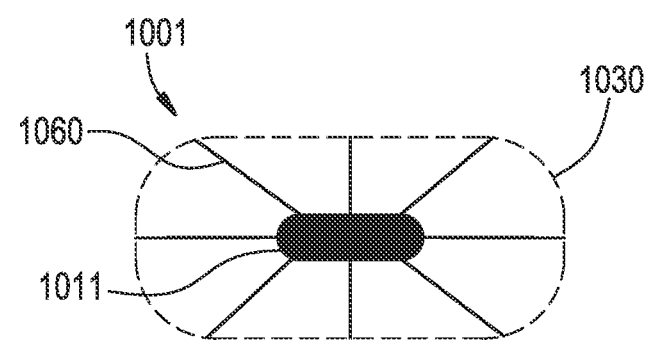

FIG. 10C shows an expanding cage 1001 that includes a fixed interior scaffold 1011 surrounded by an exterior woven textile substrate 1030 in a collapsed state. The exterior woven textile substrate 1030 can be connected to the fixed interior scaffold 1011 by a plurality of threads 1060. The fixed interior scaffold 1011 can be configured to constrain the expansion of the exterior woven textile substrate 1030 at a designed maximum extension size, as shown in FIG. 10C. In FIG. 10C, the shape of the inflated exterior woven textile substrate 1030 can be a function of the shape of the fixed interior scaffold 1011 and the length of the threads 1060.

In some instances, the threads 1060 can be inelastic. In other instances, the threads 1060 can be elastic and an inflated shape of the exterior woven textile substrate 1030 can also be a function of the elastic property of the threads 1060.

Figure 10E:
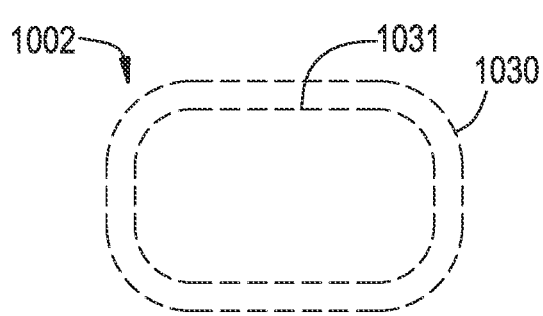
FIGS. 10E and 10F are cross-sectional schematics of two alternative expanding cage device embodiments with multiple interior chambers.
Figure 10F:
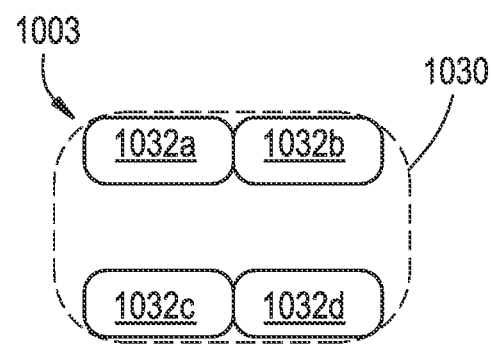

FIGS. 10E and 10F are cross-sectional schematics of two alternative expanding cage device embodiments with multiple interior chambers. FIG. 10E shows the inflatable portion of an expanding cage 1002 that includes an core inflatable structure 1031 and an exterior inflatable structure 1030. The core inflatable structure 1031 can be configured to be filled with an inflationary material and the outer inflation structure 1030 can be configured to be filled with an anti-inflammatory or other media for providing a biological effect.

FIG. 10F shows the inflatable portion of an expanding cage 1003 that includes an outer inflatable structure 1030 that includes a plurality a different chambers 1032a-d that can be inflated individually to change the overall shape of the outer inflatable structure 1030. In some instances, the different chambers 1032a-d are in fluid communication with each other. In some instances, the different chambers 1032a-d are separate from each other.

Figure 10G:
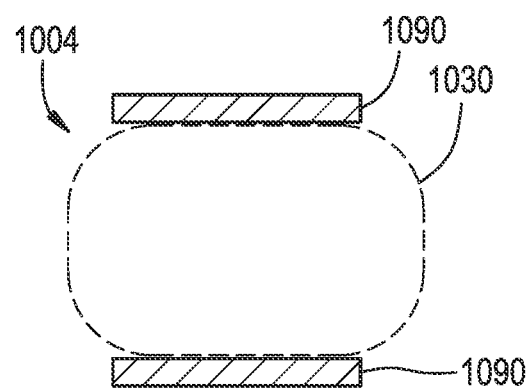
FIG. 10G is a cross-sectional schematic an alternative expanding cage device embodiment with additional structural components attached on the top and bottom face to improve fixation.

FIG. 10G is a cross-sectional schematic an alternative expanding cage device embodiment 1004 with additional structural components 1090 attached on the top and bottom face of an outer inflatable structure 1030 to improve fixation. The additional structural components 1090 can be removably attached to the outer inflatable structure 1030. The additional structural components 1090 can be configured to engage with vertebral faces.

Figure 11A:
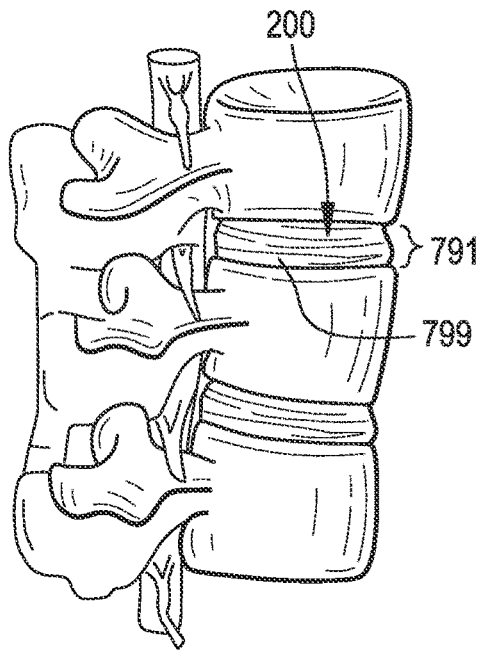
FIGS. 11A-D are illustrations of an example procedure for replacing a spinal disc with a metamaterial expanding cage device.
Figure 11B:
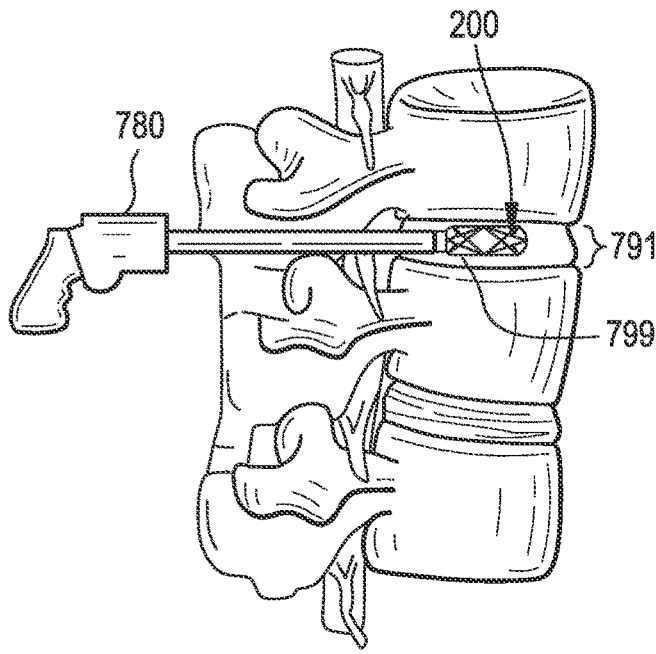
Figure 11C:
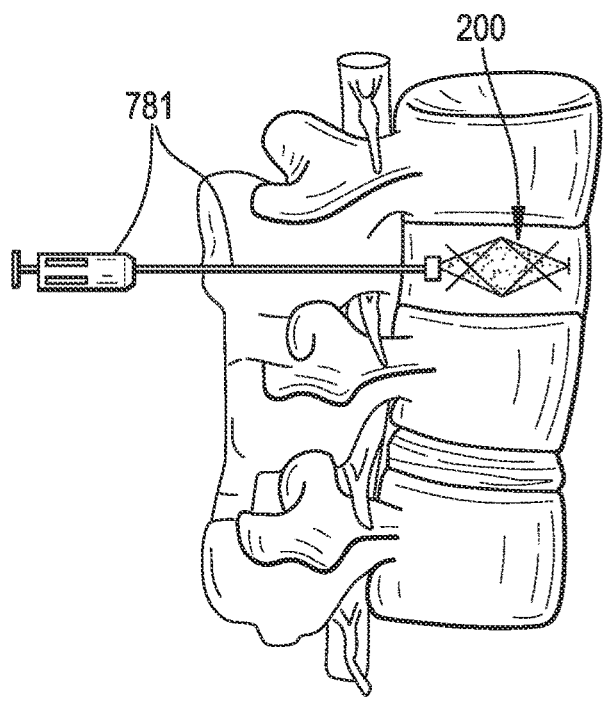
Figure 11D:
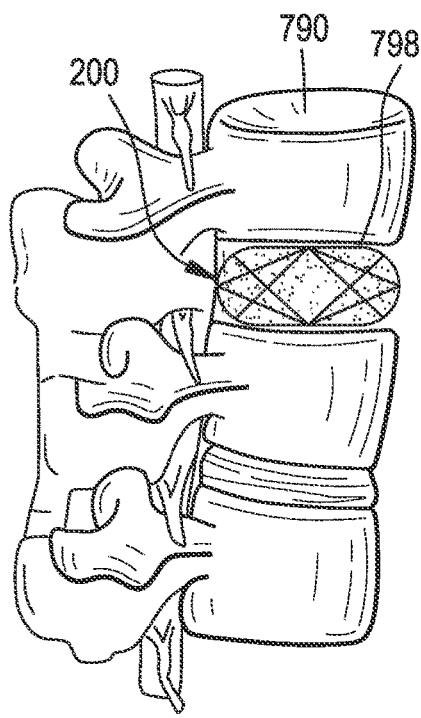

FIGS. 11A-11D are illustrations of an example procedure for replacing a spinal disc with an expanding spinal fusion cage device 200 constructed using metamaterials (e.g., 3D scaffolds 210 and a woven textile substrate 230). FIG. 11A shows a section of a patient's spine 790, where degenerated disc material 799 is removed from the intervertebral space 791. Next, as shown in FIG. 11B, the expanding spinal fusion cage 200 can be implanted and positioned in the cleared intervertebral space 791 using an implant instrument 780. Next, as shown in FIG. 11C, an inflationary medium 719 (e.g., medical cement or bone cement) can be pumped into the expanding spinal fusion cage 200 to cause the expansion of the expanding cage 200. When the expanding cage 200 is filled with the inflationary medium 719 (and, in some embodiments, following curing of the inflationary medium), it can provide a solid weight-bearing structure in the intervertebral space 791. FIG. 11D shows the patient's spine 790 post-operatively, where fusion and osteointegration have resulted in the patient's own bone matter 798 forming between the adjacent vertebrae using the woven textile substrate 230 and cured inflationary medium as a scaffold structure.

Example Materials

Existing 3D printing applications and technologies can enable 3D printing onto fabric substrates, allowing complex printed structures can be incorporated onto fabrics. For example, in the fashion industry, apparel can be 3D printed, where a combination of hard geometric shapes (e.g., 3D printed structures) and a soft, drape-able substrate (e.g., a fabric) can be combined to provide new ergonomic and aesthetic possibilities. Such techniques can allow, by way of further example, control of how a garment moves on the body through the precise design of, and interface between, the 3D printed and woven components. Additionally, such techniques can leverage 3D printing onto textiles to create programmable textiles, e.g., fabrics that have a form of shape memory.

By way of further example, in some embodiments material tracks can be printed at variable thicknesses onto a pre-stressed textile substrate. Once the textile is allowed to take its relaxed state, the printed geometry can constrain the contraction, thereby directing the fabric into a designed, pre-defined form.

In some instances, the materials for the meta-material solution can be a combination of woven polyester for the textile substrate (e.g., an expanding structure or the textile substrate 230 of FIG. 8A-8D) and a polyester composite or polyisoprene for the 3D printed scaffold (e.g., an stabilizing structure 210 or the 3D scaffold 210 of FIGS. 8A-8D). In some implementations, the materials can be biocompatible, e.g., meeting the US Pharmacopeia (USP) Class VI standards for biocompatibility (or can be formulated to meet such standards).

In some instances, cement can be used as a fixation method. For example, in some embodiment existing medical cements can be suitable. In some instances, a solid-setting compound such as medical bone cement can be used to fix the final expanded position of the expanding cage device in order to prevent maintaining a permanently inflated device in the body under pressure. In some instances, hydrogel and other gelatinous materials are used as fillers, which can be, for example, inserted at elevated temperatures and set at body temperature. In some instances, a phase change temperature of the filler material is tailored for the specific application. In some instances, an electronic device is added that heats the material to change the compressibility of the filler, which can be done, for example, in selective channels to change the local compressibility of the filler.

In some instances, the materials of the meta-material expanding cage 200 can be capable of being compressed, rolled, or folded into a small form-factor without compromising the 3D printed scaffold or without compromising the woven substrate. In some instances, the woven textile substrate 230 (e.g., the expanding structure) can be capable of expanding or unfolding at least about 280% in volume from the collapsed state to the expanded state. In some instances, the 3D printed scaffold (e.g., a stabilizing structure of the 3D scaffold 210 of FIGS. 8A-8D) can be sized and shaped to provide a degree of flexibility to allow for the expansion of the cage.

In some instances, the weave of the textile substrate (e.g., an expanding structure or the textile substrate 230 of FIG. 8A-8D) can be sized and shaped to allow for precise control over weave density to ensure that the injection of the inflationary medium (e.g., bone cement) does not escape rapidly or uncontrollably through the weave of the textile substrate. In some instances, the woven textile substrate can be constructed from polyester fibers. In some instances, the polyester fibers can have a tensile strength above about 580 MPa and an elongation factor of at least about 50% in order to support high pressures that can be experienced during the injection of bone cement.

3D Printing Techniques

Certain aspects of the present disclosure include methods of 3D printing some or all of the structures of an expanding spinal fusion cage according to embodiments disclosed herein. With regard to the above-identified metamaterial cage embodiments, multiple different 3D printing techniques can be used, including, but not limited to, fused deposition modelling, material jetting, and 3D digital weaving. Other 3D printing techniques described herein, or a combination thereof, can also be used to produce various structures of the expanding cages according to aspects of the present disclosure.

Kirchhoff-Plateau Surfaces

One example method of 3D printing for use in the manufacture of expanding spinal fusion cages, and in particular the metamaterial embodiments described above, includes the use of Kirchhoff-Plateau surfaces. In some instances, the textile substrates of the present disclosure (e.g., 230 of FIGS. 8A-8D) with or without 3D scaffolds can define or utilize a Kirchhoff-Plateau surface. Example methods using Kirchhoff-Plateau include creating a 3D structure by engineering and 3D printing a programmable 2D net, or Kirchhoff-plateau surface. The methods can include simulating and flattening the 3D components of an expanding cage design to be 3D printed in a digital design environment into a 2D net structure. Afterwards, a 3D printed geometry or system of tracks (e.g., a 3D scaffold 230) can be set onto a woven substrate (e.g., a textile substrate 230) under tension. The 3D printed structure can control the contraction and deformation of the polyester substrate once released from tension. This deformation can be programmed and simulated during the initial computer aided design (CAD) stage.

One example method of manufacturing Kirchhoff-Plateau surfaces is flat knitting a 3D net, whereby a 2D manufacturing process creates a 3D structure. Because this method first manufactures a 2D material and then forms a 3D net, as opposed to directly manufacturing a 3D structure, it provides an alternate solution to 3D printing tracks onto a conformal woven substrate. In this instance, a 3D digital object (e.g., the expanding structure or stabilizing structure of the expanding spinal fusion cage) can be flattened into a net, followed by the 2D weaving of a conformal woven substrate. Three-dimensional tracks can then be printed onto the substrate in a programmable textiles process. In some examples, a 3D knitted structure can be fabricated by weaving a flat net shape, then pulling or forming the net into the final 3D product in a secondary process. In operation, a net can be 3D printed onto a flat textile substrate under tension, and the release of the substrate from tension can result in controlled deformation of the net into the desired 3D shape. A high degree of complexity can be achieved in terms of woven structures, mechanical behaviors, and 3D geometry from a 2D knitted net.

Another example method of manufacturing Kirchhoff-Plateau surfaces involves fused deposition of thermoplastics to 3D print a scaffold or track network onto a textile substrate. This method can provide another step in functionality with 2D net shapes by programming the 3D net to take its final form independent of external force or secondary processes. A high level of complexity can be achieved through the combination of 3D printed constraint tracks and a textile substrate under tension.

Yet another example method of manufacturing Kirchhoff-Plateau surfaces is with material jetting, whereby jets of ink or other materials are used to create 3D relief structures on fabrics. In some instances, the inks can be either jetted hot and solidify as they cool or contain photo-catalyzers and be cured solid from a UV light source. In some instances, one or more materials can be jet onto a polyester substrate to achieve extremely high layer height resolution (e.g., about 14 microns) and create the complex geometries, scaffolds, and tracks of certain aspects of the expanding spinal fusion cages of the present disclosure.

Tubular Knitted Structures

Another example method of 3D printing the structures of expanding spinal fusion cages includes the use of tubular knitted structures. In some instances, the expanding structure is a woven textile substrate 230 constructed from one or more tubular knitted structures and the stabilizing structure 210 is a scaffold that is 3D printed onto the tubular knitted structures.

One example method of producing the 3D scaffold structures onto a tubular knitted structure includes using a two-stage hybrid manufacturing approach. First, a 3D knitting machine can weave a tubular structure to create a conformal balloon or pouch that makes up the tubular knitted structure. In some instances, this tubular knitted structure can be made of polyester. Afterward, the tubular knitted structure can be removed from the 3D knitting system and placed onto a mandrel, whereby a secondary 3D printing process can print a geometry of 3D scaffolds across the tubular knitted structure. The 3D printed components (e.g., the 3D scaffolds or stabilization structures 210) can function as a mechanism to control and ensure the precise expansion of the tubular knitted structure (e.g., the expanding structure) as it is inflated through the injection of medical cement or other inflationary medium.

One example method of 3D printing scaffolds onto a textile substrate is material extrusion, whereby the textile substrate can be placed onto a mandrel and a fused deposition modeling head can extrude the geometry of the 3D scaffolds onto the textile substrate of the tubular knitted structure as it rotates.

Another example method of 3D printing scaffolds onto a textile substrate is using material jetting, whereby the extrusion head of the material extrusion method noted above can be substituted with a material jetting head. Material jetting methods can provide a greater degree of precision in material deposition, layer-height resolution, and printing speed. Furthermore, the material jetting process can print in multiple materials simultaneously, which can increase the functionality of the design by providing for printing of multiple embedded materials.

An example method of 3D printing a textile substrate is using digital weaving systems to create woven substrates. Three-dimensional weaving technologies provide an ability to design and manufacture a conformal tubular woven structure to function as a bag and substrate to a secondary 3D printed track component. For example, 3D looms and weaving machines can create complicated customized tubular meshes or structures by weaving multiple filaments in 3D space. By picking up or dropping stitches, the circumference of the tube can be varied over the length of a part, thereby enabling the design of complex tubular structures. Additionally, digital weaving methods can create multi-tube and multi-branch geometries, which enable multi-branching spinal cage designs to be manufactured.

In some instances, the complex nets or balloons of the textile substrate can be alternatively manufactured in 3D using 3D electrospinning as an alternative to the textile weaving methods described above. Electrospinning can involve creating an electrical potential between a mandrel (e.g., acting as a cathode) and a fiber emitter (e.g., acting as an anode) to deposit fibers (e.g., nanofibers) over the mandrel. Electrospinning can create bioscaffolds and very fine strong fibers suitable for use as the substrate of, for example, the textile substrate 230 of the expanding cage 200 of FIGS. 8A-8D. Electrospinning a textile substrate in 3D can also enable the substitution of polyester fibers for wholly organic materials (e.g., as collagens and hyaluronic acid).

As described below, several embodiments of additive manufacturing over woven substrates can make use of a spinning mandrel to hold the substrate while additional material is deposited thereon. In some embodiments, rather than using a rotating cylinder, cuboid, or spherical shape to create an expandable section of a cage, 3D printing or additive manufacturing could be used to create a mandrel of a desired shape, e.g., a geometrically-complex mandrel that could be, e.g., asymmetric in some respect, etc. With reference to electrospinning in particular, a conductive layer could be added to the mandrel to create a cathode and enable fiber deposition. Use of 3D printed mandrels, with electrospinning or any of the other deposition techniques described herein, can allow more complex expandable section shapes.

3D Printing Processes

Below is exemplary description regarding various embodiments of 3D printing or additive manufacturing processes that can be used to manufacture the above-described embodiments of expanding cage devices.

FIGS. 12A-C illustrate an example extrusion process for manufacturing an expanding cage device. FIGS. 12A-C show a production apparatus 1200 for an extrusion process, using a 3D printing system 1220 and a separate part cleaning station 1290. The 3D printing system 1220 can include a build chamber 1207, a suspension or support material 1206, an extrusion apparatus 1204 contain polyisoprene 1203, and a computer 1201 controlling the 3D printing system 1220. In some instances, the 3D printing system 1220 can ensure that the support containments 1205 are within acceptable tolerances.

In operation, the computer 1201 can convert a CAD model to build instructions, which can be transmitted 1202 to the 3D printing system 1220, where a printed part 1208 can be created. Afterwards, the extrusion apparatus 1204 can be removed 1209 and the completed part 1210 can be allowed to cure before being transferred to the cleaning station 1290. In the cleaning station 1290, remaining support material 1212 can be removed with a manual cleaning tool 1291 as well as with cleaning fluid 1293 dispensed from cleaning jet nozzles 1292.

FIGS. 13A-C illustrate an example material jetting process for manufacturing an expanding cage device. FIGS. 13A-C show a production apparatus 1300 for a material jetting process using a 3D printing system 1320 and a separate part cleaning station 1290. The 3D printing system 1320 includes a build plate 1306, a build material delivery apparatus 1303, a support material delivery apparatus 1305, a supply 1304 of the materials, and a computer 1201 controlling the 3D printing system 1320.

In operation, the computer 1201 can convert a CAD model to build instructions, which can be transmitted via a connection 1202 to the 3D printing system 1320, where a printed part 1308 can be created on the build plate 1306 using a material jetting method. Afterwards, the printed part 1308 can be removed 1309 and transferred to the cleaning station 1290.

Figure 14A:
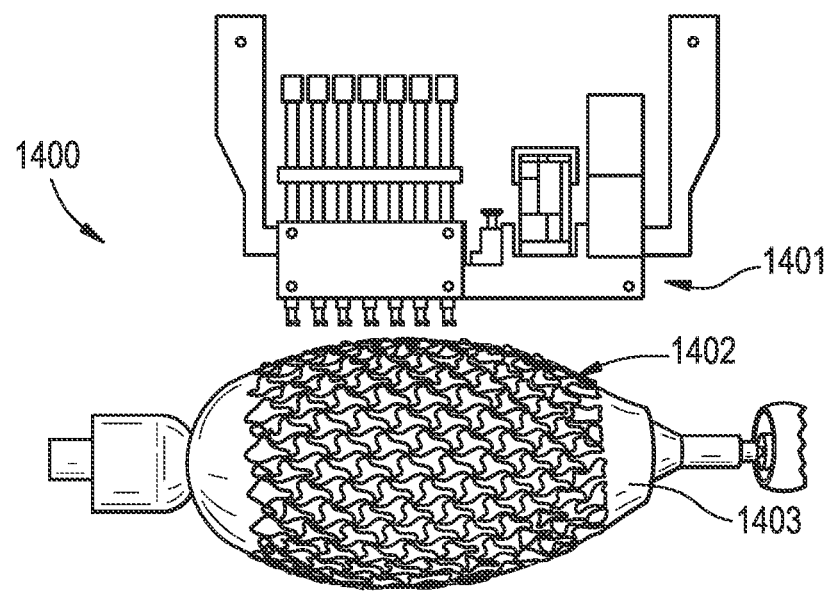
FIGS. 14A and 14B are illustrations of an example process for manufacturing a woven tubular structure for use in an expanding cage device.
Figure 14B:
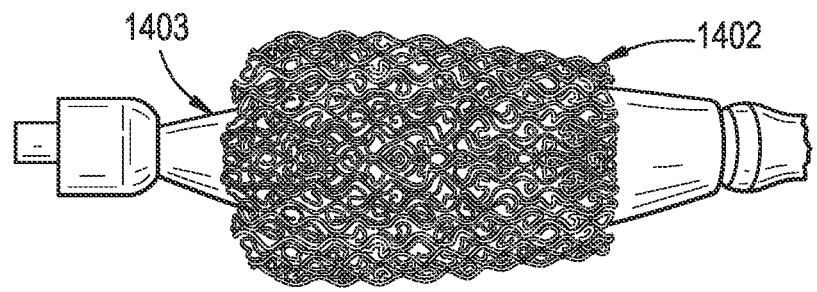
Figure 15A:
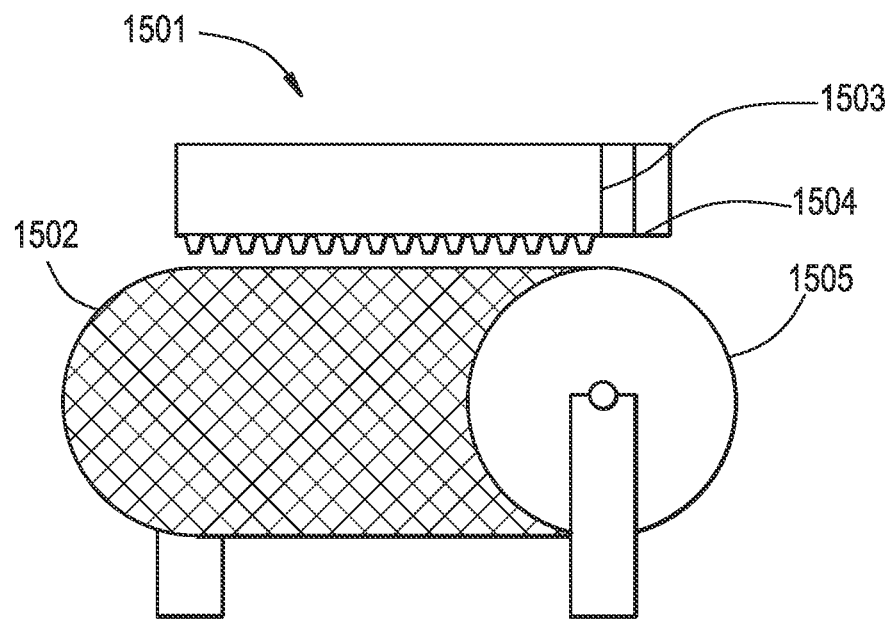
Figure 15B:
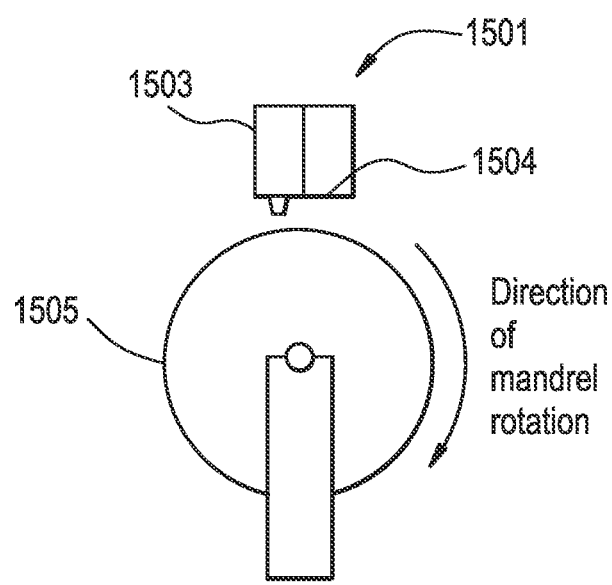
Figure 16A:
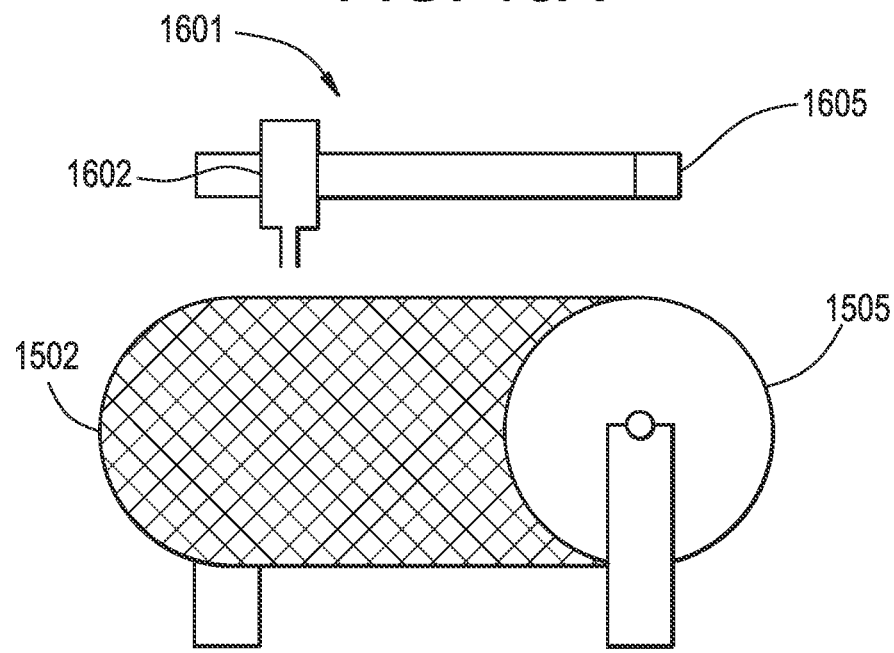
FIGS. 16A-E are illustrations of an example process for manufacturing an expanding cage device.
Figure 16B:
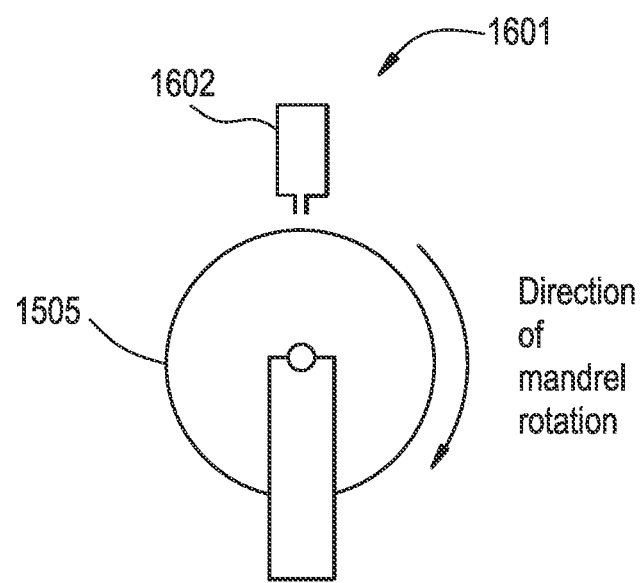
Figure 16C:
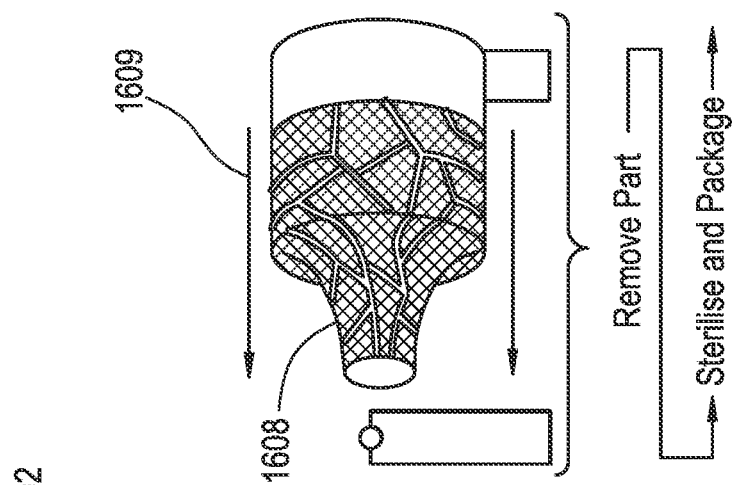
Figure 16D:
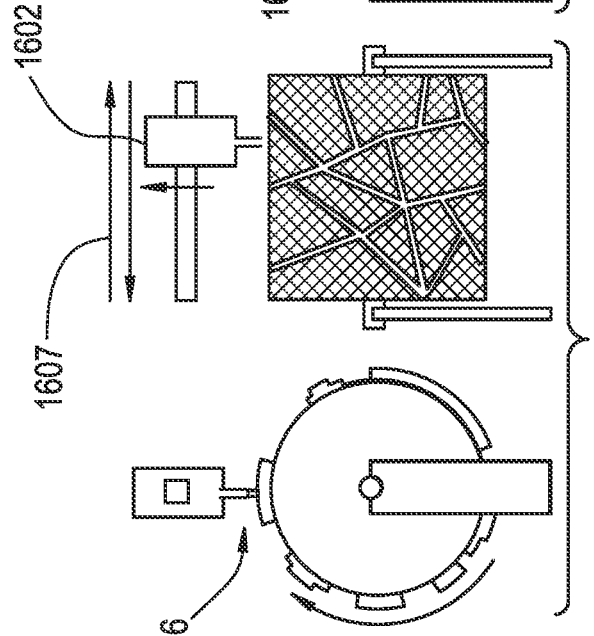
Figure 16E:
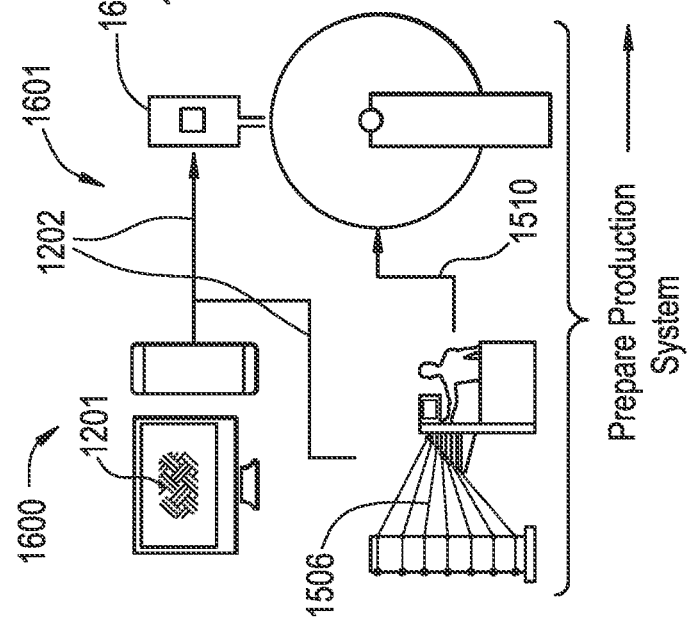

FIGS. 14A and 14B illustrate an example process for manufacturing a woven tubular structure for use in an expanding cage device. FIG. 14A shows a tubular knitted structure 1402 being printed by a material jetting apparatus 1401 onto an inflated substrate 1403 in an expanded configuration. FIG. 14B shows the tubular knitted structure 1402 in a collapsed state after the substrate 1403 has been deflated in order to remove the tubular knitted structure 1402.

FIGS. 15A-E illustrate an example process for manufacturing an expanding cage device. FIGS. 15A-E show a 3D printing system 1501 for use in a meta-material jetting process 1500 that is designed to work with existing 3D weaving systems for fabricating a woven substrate 1502. The 3D printing system 1501 includes a mandrel 1505 holding a woven substrate 1502 (e.g., a polyester substrate in some embodiments) and a printing apparatus including jetting heads 1503 and curing heads 1504.

In operation, a computer 1201 can convert a CAD model to build instructions for both woven substrate fabrication and 3D scaffold track fabrication, which can be transmitted (e.g., via connection 1202) to the 3D printing system 1501 and a 3D weaving system 1506. The 3D weaving system 1506 can attach the fabricated woven substrate to the mandrel 1505 of the 3D printing system 1501, where the jetting heads 1503 can jet polyisoprene or other materials onto the mandrel 1505 and the curing heads 1504 can cure the freshly jetted polyisoprene or other materials as the mandrel rotates underneath the printing apparatus. Each rotation can lay down a single layer of polyisoprene or other material, and the printing apparatus can be raised 1507 with each full rotation. After the 3D printing is completed, the completed 3D printed part 1508, which can include the printed tracks and the woven substrate 1502 to which they are attached, can be removed 1509. The part 1508 can contract as it is removed from tension around the mandrel 1505.

FIGS. 16A-E illustrate an example process for manufacturing an expanding cage device. FIGS. 16A-E show a 3D printing system 1601 for use in a meta-material extrusion process 1600 that is designed to work with existing 3D weaving systems for fabricating a woven substrate 1502. The 3D printing system 1601 can include a mandrel 1505 holding the woven substrate 1502 (e.g., a polyester substrate in some embodiments) and a printing apparatus including an extrusion head 1602 that can travel on an extrusion head gantry 1605 and contain the 3D printing material 1602.

In operation, a computer 1201 can convert a CAD model to build instructions for both woven substrate fabrication and 3D scaffold track fabrication, which can be transmitted (e.g., via connection 1202) to the 3D printing system 1601 and a 3D weaving system 1506. The 3D weaving system 1506 can attach the fabricated woven substrate to the mandrel 1505 of the 3D printing system 1601, where the extrusion head 1602 can print the tracks 1606 onto the woven substrate 1502 by moving 1607 along the gantry 1605, and being indexed away from the mandrel 1505 after each layer is printed. After the 3D printing is completed, the completed 3D printed part 1608, which includes the woven substrate 1502 and the printed tracks 1606, can be removed 1609. The part 1608 can contract as it is removed from tension around the mandrel 1505.

Other Alternatives

In addition to the above-described materials that can be utilized to create the expanding cage devices described herein, other materials can be utilized in some embodiments. For example, in some embodiments certain metallic materials can be utilized with the above-described processes. Examples of such materials can include stainless steel, cobalt-chromium, titanium, tantalum, and nitinol, among others.

Moreover, in some embodiments additional features can be integrated with the 3D printed components described herein. For example, additively manufactured components can be individually tracked using unique identifiers, such as geometric keys or tags printed into the product. In the case of a tag, for example, a unique serial number, QR (quick response) code, or other identifier can be automatically printed on a tag incorporated into the structure, or on any surface of the structure. Still further, parts can be printed with reliefs to accommodate RFID (radio frequency identification) tags or other types of tracking components.

In some embodiments, the filler materials can comprise multiple materials so that elastic properties of the filler material can be adjusted as well. For instance, creating an emulsion of bone cement and either a liquid or a fluid can alter the modulus of the final cured state of the cement. In addition, some embodiments include incorporating elastomeric or ceramic beads in the mix, which can achieve similar results by altering the modulus of the final cured state of the cement.

In addition to being directed to the specific combinations of features claimed below, the present disclosure is also directed to embodiments having other combinations of the dependent features claimed below and other combinations of the features described above.

One skilled in the art will appreciate further features and advantages of the disclosure based on the above-described embodiments. Accordingly, the disclosure is not to be limited by what has been particularly shown and described, except as indicated by the appended claims. This description will suggest many variations and alternatives to one of ordinary skill in this art. All these alternatives and variations are intended to be included within the scope of the claims. Those familiar with the art may recognize other equivalents to the specific embodiments described herein and such equivalents are also intended to be encompassed by the claims. All publications and references cited herein are expressly incorporated herein by reference in their entirety.

What is claimed is:

1. An intervertebral disc implant, comprising:
an expandable cage assembly configured to expand from a collapsed state to an expanded state in an intervertebral space when inflated with a material, the expandable cage assembly comprising:
an inflatable section defining an interior volume configured to receive the material and expand the interior volume in response to a pressure from the received material to cause the expandable cage assembly to transition from the collapsed state to the expanded state, and
a stabilization section configured to restrain the inflatable section during inflation,
wherein the inflatable section comprises a textile substrate, and
wherein the stabilization section comprises a 3D scaffold that is printed onto the textile substrate and configured to restrict further expansion of the textile substrate in the expanded state.

2. The intervertebral disc implant of claim 1, wherein the stabilization section at least partially surrounds the inflatable section, the stabilization section sized and shaped to define at least a portion of a periphery of the expandable cage assembly.

3. The intervertebral disc implant of claim 1, wherein at least one of the inflatable section and the stabilization section comprises a 3D printed material.

4. The intervertebral disc implant of claim 1, wherein the 3D scaffold comprises a single-piece structure.

5. The intervertebral disc implant of claim 4, wherein the single-piece structure comprises a 3D printed material.

6. The intervertebral disc implant of claim 1, wherein at least one of the inflatable section comprises a porous structure configured to allow interaction between the material and the intervertebral space.

7. The intervertebral disc implant of claim 1, wherein the stabilization section comprises a rigid structure.

8. The intervertebral disc implant of claim 1, wherein at least one of the inflatable section and the stabilization section comprises a bio re-absorbable material configured to be reabsorbed into the body after a time when fusion has taken place.

9. The intervertebral disc implant of claim 1, wherein at least one of the inflatable section and the stabilization section comprises embedded organic materials configured to expedite osteointegration.

10. The intervertebral disc implant of claim 9, wherein the embedded organic materials include at least one of: hyaluronic acids, collagens, proteins, patient cells from bone grafts.

11. The intervertebral disc implant of claim 1, wherein at least one of the inflatable section and the stabilization section comprises an embedded active pharmaceutical compound.

12. The intervertebral disc implant of claim 1, wherein the expandable cage assembly is formed from a plurality of materials.

13. The intervertebral disc implant of claim 1, wherein the inflatable section and the stabilization section are formed from different materials.

14. The intervertebral disc implant of claim 1, comprising at least one additional structural component attached thereto, wherein the additional structural component is configured to improve fixation in the intervertebral space.

15. The intervertebral disc implant of claim 1, wherein the 3D scaffold is configured to control a differential expansion rate of the textile substrate during an inflation process of the intervertebral disc implant from the collapsed state to the expanded state.

* * * * *